(12) United States Patent
Dirks et al.

(10) Patent No.: US 8,692,067 B2
(45) Date of Patent: *Apr. 8, 2014

(54) REVERSE BREEDING

(75) Inventors: Robert Helene Ghislain Dirks, Oudenbosch (NL); Cornelis Maria Petrus Van Dun, Roosendaal (NL); Kornelius Reinink, Delft (NL); Jacobus Petrus Cornelis De Wit, Oudenbosch (NL)

(73) Assignee: Rijk Zwaan Zaadteelt en Zaadhandel B.V., De Lier (NL)

( * ) Notice: Subject to any disclaimer, the term of this patent is extended or adjusted under 35 U.S.C. 154(b) by 0 days.

This patent is subject to a terminal disclaimer.

(21) Appl. No.: 13/253,697

(22) Filed: Oct. 5, 2011

(65) Prior Publication Data

US 2012/0131688 A1    May 24, 2012

Related U.S. Application Data

(63) Continuation of application No. 10/487,468, filed as application No. PCT/EP02/09526 on Aug. 23, 2002, now Pat. No. 8,242,327.

(30) Foreign Application Priority Data

Aug. 23, 2001  (EP) .................................. 01203193
Feb. 12, 2002  (EP) .................................. 02075582

(51) Int. Cl.
- *A01H 1/00*    (2006.01)
- *C12N 15/82*   (2006.01)
- *C12N 15/87*   (2006.01)
- *C07H 21/04*   (2006.01)

(52) U.S. Cl.
USPC ........... 800/285; 800/286; 800/278; 536/24.5

(58) Field of Classification Search
USPC ........................................... 800/285
See application file for complete search history.

(56) References Cited

U.S. PATENT DOCUMENTS

| 5,908,973 A | 6/1999 | Abu-Bakar et al. |
| 6,660,849 B1 * | 12/2003 | Dehesh ............... 536/23.6 |
| 8,242,327 B2 * | 8/2012 | Dirks et al. ............ 800/285 |

FOREIGN PATENT DOCUMENTS

JP    11-318249    11/1999

OTHER PUBLICATIONS

Dirks et al., "Reverse breeding: a novel breeding approach based on engineered meiosis," Plant Biotechnology Journal (2009) &, pp. 837-845.
Mathilde Grelon, et al., AtSP011-1 Is Necessary for Efficient Meiotic Recombination In Plants, EMBO Journal (2001) vol. 20, No. 3, p. 589-600.
"Plant breeding" www.wikipedia.org/wiki/Plant_breeding.
Jeffrey L. Salisbury, et al., Centrosomes and Cancer, Biology of the Cell (1999) vol. 91, p. 451-460.
Schaart, "Novel plant breeding techniques" report commissioned by COGEM, www.cogem.net/ContentFiles.
Y. Wan, et al., Effect of Chromosome-Doubling Agents on Somaclonal Variation in the Progeny of Doubled Haploids of Maize, Plant Breeding (1995) vol. 114, p. 253-255.
Wjinker et al., "Managing meiotic recombination in plant breeding" Trends in Plant Science, vol. 13, No. 12, pp. 640-646, available online Oct. 22, 2008.
Link et al, "An Approach to Genetic Improvement of Clonal Cultivars via Backcrossing," Crop Science, vol. 35, No. 3, p. 931 (1995).

* cited by examiner

*Primary Examiner* — Li Zheng
(74) *Attorney, Agent, or Firm* — Vedder Price P.C.; Thomas J. Kowalski; Deborah L. Lu

(57) ABSTRACT

A method for efficiently producing homozygous organisms from a heterozygous non-human starting organism, comprising providing of a heterozygous starting organism; allowing the starting organism to produce haploid cells; creating homozygous organisms from the haploid cells thus obtained; and selecting the organisms having the desired set of chromosomes, wherein during production of the haploid cells no recombination occurs in order to obtain a limited number of genetically different haploid cells. Recombination can also be prevented or suppressed.

7 Claims, 16 Drawing Sheets

Figure 1

AAGAGGCTTTTGGGGAATTTAGGTCTGGGAAAACTCAATTAGCACATACCCTTTGTGTCA
CCACGCAGCTGCCTACAAGCATGAAAGGTGGGAATGGGAAAGTGGCTTACATTGACACTG
AGGGAACCTTCCGCCCTGATCGGATTGTCCAAATTGCTGAAAGATTTGGAATGGATCCCG
GAGCTGTGCTTGACAATATCATTTATGCTCGTGCTTACACCTATGAGCATCAGCACAACT
TGCTTCTTGGCCTTGCTGCAAAAATGTCCGAGGAACCATTTAAGATTCTGATTGTTGACT
CAATCATTGCTTTATTCCGAGTGGATTTCACTGGAAGAGGAGAACTCGCAGACCGCCAGC
AAAAACTAGCTCAGATGCTT

Figure 2

ACAGAGGCTTTTGGGGAATTCAGGTCTGGGAAAACTCAGTTAGCACATACCCTTTGTGTC
ACCACGCAGCTGCCTACAAGCATGAAAGGTGGGAATGGGAAAGTGGCTTACATTGACACT
GAAGGAACCTTCCGCCCTGATCGAATCGTCCCCATTGCTGAAAGATTTGGAATGGATCCA
GGAGCTGTGCTTGACAATATCATCTATGCTCGTGCTTACACCTATGAGCATCAGTACAAC
TTGCTTCTTGGCCTTGCTGCAAAAATGTCTGAGGAACCATTTAAGATTCTGATTATTGAC
TCGATCATTGCTTTATTCCGAGTTGATTTCACTGGAAGAGGGGAACTCGCAGACCGCCAG
CAAAAACTAGCTCAGATGCTT

Figure 3

AGAGGCTTTTGGGGAATTCAGGTAAGGATCAATCAAATATTGTATTAACCTTGTGGTAGA
GCTTTAGTAGAATATTTCATCTAACTCTGCTGTATGAACTATTTATTCAGATCTGGAAAG
ACACAACTTGCTCATACTCTCTGTGTCTCTACTCAGGTTCAGCTCTGATCTTAGTCAGAA
GCAATGGAACATCATTACCGTCTAGATTACTTCTGATCCTTTATATGCTTTATGCTGAAT
CATGATATCATTCGGAGTTTAACAAGATTGCCAATTGATTTGTCTGATTTACTGCAGCTT
CCGACTAGTATGAAAGGAGGGAATGGAAAAGGTGGCTTACATTGATACTGAGGGAACATT
GTATCCTTGCTAATATTTCGCAACTCATGAAAATTCAAACTAGCACCTATTACTCTCTTC
ATTAAGTAGCAGCTGCAGAAACTCAAGTGAATGCTGCTTCCTTCCATTTTATCTTTTTTC
CTCAACCAAAGCGTACTACAGTCGGCCAGATCGTGTTGTTCCCATTGCTGAAAGATTTGG
AATGGACGCTGGAGCAGTTCTTGACAATGTAAAGGGTCTTTTACACCCACCATTTAATCA
TCTACTGCTCTTTGTTTAGTGTACTGATTTCTTATCCTTTCTTTCCTTATTATGTGATCA
GATCATTTATGCTCGCGCATACACATATGAACATCAATATAACCTGCTTCTTGGTCTGGC
AGCAAAAATGGCTGAAGAGCCTTTCAGACTTCTGGTGAAAGCCACATCATCTGCTTTATC
TTGAATAAGACCATTACTGGCGGCAGTTGTCTCAGATACTGAAATTTTACTTGCAGATTG
TTGACTCTGTGATTGCTTTATTTCGAGTGGATTTCACTGGAAGAGGAGAGCTTGCAGACC
GTCAGGTATAACTAAATACACAAGCATAATATTTGATTAATTAAAAACCTATCTCTGATA
TTTATCTGTGTTGAGAAGAACCTGCAATCACCTGTTCTGGTAGACTTTTTCTGAATGCTT
ATGCCTTCTTGCCATTTCAGCAAAAACTAGCTCAGATGCTT

Figure 4

```
ACAGAGGCTTTTGGGGAATTCAGGTAAGGATCAACTAACTATTGCTTTAGCTTTGTGGTA
GAAGCATTAGTAGAATTTTACATCTAACTGTCTGAATGAACTATTTATTCAGATCTGGAA
AGACACAACTTGCTCATACTCTCTGTGTCTCTACTCAGGTTCACCTCTGATCTTAGTCAG
AAGCAATGGAACATCTTTACCTTCTAGATTACTCCTGATCCTTTATATGCTTTATGCTTA
ATCATGGTATCATCCTGAATTTAACAAGATTGCCAATTGATTTGTCTGGTTTATTGCAGC
TTCCTACAAGCATGAAAGGAGGGAATGGAAAGGTGGCTTACATTGACACCGAGGGAACATTG
TATCCTTGCTAATATTTCTCTACTCATACAGCATGAACTACAAACTAGCTCCTATTAG
TCTCTTCACTAAGTAGCAGCTGCAGAAGCTCAAGAGAATTCTTCCCTTCCTATATTTTC
CCTCAACTAAGTGTACTATAGTCGGCCAGATCCGTGTGGTGCCCATTGCTGAAAGATTTG
GAATGGACGCAGGAGCAGTTCTTGACAATGTTAAGTGTCTTTTATTCACTCATTTAATCA
TCTACTGCTCTTTGTTCAGCGTACTGATTTCTCAGCTGATTTTCTAATCCTTCCTTTCCTAA
TCACGTGAATGAATCAGATCATTTATGCTCGCGCATACACATACGAACATCAATACAACTTG
CTTCTTGGTTTGGCAGCAAAAATGGCTGAAGAGCCTTTCAGACTTCTGGTGAAAGCCACAAC
TTCTGGTTTATCCTGAATAAGTCCATTACTGATGGCAGTTGTCTCAGATACTGAAATTTTAC
TTGCAGATCATTGACTCCGTGATTGCTTTATTTCGAGTGGATTTCACTGGAAGAGGAGAGCT
TGCAGATCGCCAGGTATGAAATACAGAGCATGATAGCTGATTTATTAAGTTCCCATTTATTG
CTATTTACGGTTGTGTTAAGAAGACCTGCAATCACCTGTTCTGATGTGCTATCTTTTGAATG
CCTACACTTTGTTGCCATTTACAGCAAAAACTAGCTCAGATGCTT
```

Figure 5

```
AGAGGCTTTTGGGGAATTCAGGTAACAATCAACTAATTATCGTTTTACCTTTGGTGTAGA
AGCATTATCTGAATATTTCATCTAACTCTCTGCTGAATGAACAATTTATTCAGATCTGGA
AAGACACAACTTGCTCATACTCTATGTGTCTCTACTCAGGTTCACCTCTGATCTTAGTTA
GAAGCAATGAAGTTTTTGACCTTCTAAATCCCTCCTTATCCTTTATATGCTTTAGACTTA
ATCATGGTATCATCCAGAACATGACAAGAGTGTCAATTCGTTTGTCTGATTTATTTCAGC
TTCCTACTAGCATGAAAGGAGGGAATGGAAAGGTGGCTTACATTGATACTGAGGGAACGT
TGTATCCTTGCTGATATTCCTTACTCATGTAGCATCAATAATCAAACTAGCACTTAAAA
GTCTCCTCATGAAGTAGCAGCTGTAGAAACAAAAGAGAATGCTTCCTTCCATTTTATCTT
GTTTCTTCAACCTAAGTGTACTATAGTCGGCCAGATCGTCTTGTGCCCATTGCTGAAAGA
TTTGGAATGGACGCAGGAGCTGTTCTTGACAATGTAAAGCGTCTTTTGACCCTCATTTAA
TGATCTCTCCCTCTCTTTGTTTAGCTTACTGATTTTTCAGCTGATTTCTTATCATTCCCT
TTTCCCCTTATGATGTGAATTCACCAGATCATTTATGCTCGTGCATACACATACGAACAT
CAGTACAGCCTGCTTTTTGGTCTGGCAGCAAAAATGGCTGAAGAGCCTTTCAGACTTCTG
GTGAAAGCCACAACTTCCAGTTTATCCTGAATAGAATCATTGCTAATGGACTCATATACT
GAAATATTACTTGCAGATTGTTGACTCTGTGATTGCTTTATTTCGAGTGGATTTCACTGG
AAGAGGAGAACTTGCAGAACGTCAGGTATAACAAAATACAGAAATATGATATTTGATTTA
TAAGTTCCTGTCTCTTGATATTTATCTTTGTTCTAAGAAGAGCCTGCAATCACCTATTCT
AAATATGTTTTAATTTGAGTGACTGCACCTTCTTGCCATATCCAGCAAAAACTAGCTCTG
ATGCTT
```

Figure 6

AACGGGTTGGTGATGGGGTGGTTAAAGTTTAGGGAAGCTGGAAGGAAGTTTGATTGTTTA
AGCAGCCTGAATACTGCATTTCCCGTTCCTGTTCTTGTAGAGGAAGTCGAAGATATTGTT
AGTTTGGCAGAGTACATACTGGTGGTGGAAAAGGAAACAGTATTCCAGCGTTTAGCAAAT
GACATGTTTTGCAAGACGAACCGCTGCATCGTCGTCACAGGAAGAGGCTATCCTGATGTC
TCTACAAGAAGGTTCTTGCGACTCCTGATGGAGAAGTTGCAACTACCTGTGCATTGTCTA
GTTGACTGTGATCCATATGG

Figure 7

AACGGGTTGGTGATGGGGTGGTTAAAGTTTAGGGAAGCTGGAAGGAAGTTTGATTGTTTA
AGCAGCCTGAGTACTGCATTTCCCGTTCCTGTTCTTGTAGAGGAAGTCGAAGATATTGTT
AGTTTGGCAGAGTACATACTGGTGGTGGAAAAGGAAACAGTATTCCAGCGTTTAGCAAAT
GACATGTTTTGCAAGACGAACCGCTGCATCGTCGTCACAGGAAGAGGCTATCCTGATGTC
TCTACAAGAAGGTTTTTGCGACTCCTGATGGAGAAGTTGCAACTACCTGTGCATTGTCTA
GTTGACTGTGATCCATAT

Figure 8

GTTTTTTATGGCTCATATTGGATGTTTTGTCCCGGCTGCATCGGCCAAAATCGGCCTAGCCA
GAGAGATTTTCACGCGACTCTATTCGGAAGAGTCGACGCACAACAGCCAGTCGTCATTCCAG
TTGGAATTGATACAAATGAGTCGAATATTGTCATCGTCGTCGGACCGGTCACTGATTTTGAT
TGACGAATTCGGAAAGGGAACTAATACTGTGGATG

Figure 9

```
>gi|1582703|prf||2119252A   MSH5 gene [Saccharomyces cerevisiae]
           Length = 901

Score = 62.0 bits (149), Expect = 2e-09
 Identities = 29/72 (40%), Positives = 44/72 (60%)
 Frame = +2

Query: 5     FMAHIGCFVPAASAKIGLAREIFTRLYSEESTHNSQSSFQLELIQMXXXXXXXXXXXXXX 184
             ++A IGCFVPA  A+IG+A +I TR+ ++E+ + +QSSF L+   QM
Sbjct: 661   YLAQIGCFVPAEPARIGIADKILTRIRTQETVYKTQSSFLLDSQQMAKSLSLATEKSLIL 720

Query: 185   XXEFGKGTNTVD 220
             E+GKGT+ +D
Sbjct: 721   IDEYGKGTDILD 732

>gi|3108220|ab|AAC62533.1|
http://www.ncbi.nlm.nih.gov/LocusLink/list.cgi?Q=3108220[pgi]"TYPE=PICT;ALT=LocusLi
nkinfo"http://www.ncbi.nlm.nih.gov/LocusLink/list.cgi?Q=3108220[pgi]  (AF048986)
MutS homolog 5 [Homo sapiens]
           Length = 834

Score = 59.7 bits (143), Expect = 8e-09
 Identities = 32/72 (44%), Positives = 40/72 (55%)
 Frame = +2

Query: 5     FMAHIGCFVPAASAKIGLAREIFTRLYSEESTHNSQSSFQLELIQMXXXXXXXXXXXXXX 184
             FMA +G FVPA  A+IG    IFTR++S ES     S+F ++L Q+
Sbjct: 610   FMALVGSFVPAEEAEIGAVDAIFTRIHSCESISLGLSTFMIDLNQVAKAVNNATAQSLVL 669

Query: 185   XXEFGKGTNTVD 220
             EFGKGTNTVD
Sbjct: 670   IDEFGKGTNTVD 681

>gi|5814102|gb|AAD52100.1|     (AF107355) MSH5 [Mus musculus]
           Length = 258

Score = 58.2 bits (139), Expect = 2e-08
 Identities = 31/72 (43%), Positives = 41/72 (56%)
 Frame = +2

Query: 5     FMAHIGCFVPAASAKIGLAREIFTRLYSEESTHNSQSSFQLELIQMXXXXXXXXXXXXXX 184
             FMA +G FVPA  A+IG+    IFTR++S ES     S+F ++L Q+
Sbjct: 141   FMALVGSFVPAEEAEIGVIDAIFTRIHSCESISLGLSTFMIDLNQVAKAVNNATEHSLVL 200

Query: 185   XXEFGKGTNTVD 220
             EFGKGTN+VD
Sbjct: 201   IDEFGKGTNSVD 212

>gi|11359791|pir||T43201    MutS protein homolog - Caenorhabditis elegans (fragment)
   gi|3831701|gb|AAC70065.1|   (AF070070) MutS homolog [Caenorhabditis elegans]
           Length = 933

Score = 52.4 bits (124), Expect = 1e-06
 Identities = 26/70 (37%), Positives = 38/70 (54%)
 Frame = +2

Query: 5     FMAHIGCFVPAASAKIGLAREIFTRLYSEESTHNSQSSFQLELIQMXXXXXXXXXXXXXX 184
             F++HIG FVPA  AKIG+  I TR+++ +S +   S+F ++ Q+
Sbjct: 657   FLSHIGSFVPARHAKIGIVDRIVTRMFTVDSVLDGMSTFAKDVEQVALALRKATGNSLVI 716

Query: 185   XXEFGKGTNT 214
             EFGKGT T
Sbjct: 717   IDEFGKGTMT 726
```

Figure 13

```
TGTCCCGGCTGCACGGCCAAAATCGGCCTAGCCAGAGAGATTTTCACGCGACTCTATTCGGA
AGAGTCGACGCACAACAGCCAGTCGTCATTCCAGTTGGAATTGATACAAATGAGTCGAATAT
TGTCATCGTCGTCGGACCGGTCACTGATTTTGATTGACGAATTC
```

Figure 14

TGTCCCGGCTGCGCCAAAATCGGCCTAGCCAGAGAGATTTTCACGCGACTCTATTCGGAA

GAGTCGACGCACAACAGCCAGTCGTCATTCCAGTTGGAATTGATACAAATGAGTCGAATA

TTGTCATCGTCGTCGGACCGGTCACTGATTTTGATTGACGAATTC

Figure 15

```
TGTCCCGGCGCATCGGCCAAAATCGGCCTAGCCAGAGAGATTTTCACGCGACTCTATTCG
GAAGAGTCGACGCACAACAGCCAGTCGTCATTCCAGTTGGAATTGATACAAATGAGTCGA
ATATTGTCATCGTCGTCGGACCGGTCACTGATTTTGATTGACGAATTC
```

Figure 16

TGTCCCGGCTGCATCGGCCAAAATCGGCCTAGCCAGAGAGATTTTCACGCGACTCTATTC

GGAAGAGTCGACGCACAACAGCCAGTCGTCATTCCAGTTGGAATTGATACAAATGAGTCG

AATATTGTCATCGTCGTCGGACCGGTCACTGATTTTGATTGACGATTC

REVERSE BREEDING

The present application is a continuation of U.S. patent application Ser. No. 10/487,468 filed Apr. 3, 2006 now U.S. Pat. No. 8,242,327 which is a national stage application of International Application No. PCT/EP02/09526, filed on Aug. 23, 2002, published as WO 03/017753 on Mar. 6, 2003, and claiming priority to European Patent Application Nos. 02075582.3 filed Feb. 12, 2002 and 01203193.6 filed Aug. 23, 2001.

FIELD OF THE INVENTION

This invention relates to a method for efficiently producing homozygous organisms from a heterozygous non-human starting organism. The invention relates in particular to the use of this method in plant breeding to produce parental lines for the production of hybrid offspring. The invention further relates to DNA constructs for use in this method, to primer pairs to select genes for use in this method, to F1 hybrid organisms obtainable by crossing organisms that are the result of the method and to seeds resulting from the method.

BACKGROUND OF THE INVENTION

Plant breeding is one of the oldest accomplishments of man. It began when he domesticated plants were domesticated by growing them under controlled conditions and selecting those types that provided a dependable source of food. The most important feature contributing to high yield of many new varieties is their hybrid nature. The most dramatic example is hybrid corn, which was first introduced in significant amounts in 1932 and now makes up about 95% of the acreage of corn in the United States. Hybrid varieties are now available in crops such as sorghum, sugar beet, sunflower, onions, castor beans, oilseed rape, leek, cucumber, tomato, spinach, melon, pepper, carrot, cabbage, cauliflower, broccoli, radish, egg plant etc., in fungi, such as mushrooms, and in animals, such as poultry and fish.

J. Sneep and A. Hendriksen (1979, Pudoc, Centre for Agricultural Publishing and Documentation Wageningen), teach several methods for plant breeding which have been successfully applied during the last decades and which result in the varieties that are grown nowadays. In the Chapter "Current breeding methods", J. Sneep and A. Hendriksen (1979) (supra, pp 104 233), describe general breeding techniques but also the specific breeding technologies for a number of crops, such as potato, sugar beet, maize, sunflower etc.

In general, selections are made from a collection of plants that can be derived from seeds from the market (commercial varieties), gene bank accessions, land races etc. From this collection, the "best" plants are selected and crossed according to the art. So traditionally, pure lines or homogenous populations are obtained by breeding.

Plant breeding has the objective to produce improved crop varieties based on the exploitation of genetic variation, which exists within the germ plasm of a plant species. Genetic variation is traditionally obtained by crossing two genetically distinct plants to create hybrid progeny. The genotype of a progeny plant is the result of the combination of the genotypes of the male and female gamete, which through fusion resulted in a zygote, from which ultimately the progeny plant developed. Gametes are formed by the gametophytic generation during the life cycle of a plant and therefore the genetic variation of the gametes is reflected in the genotypes of the gametophytes. Gametophytes differentiate from spores, which are produced by the sporophytic generation during the life cycle of the plant. Spores are produced from differentiated cells in the reproductive organs of a plant through a specialized cell division process called meiosis.

During meiosis chromosomal segregation and recombination are the processes which cause independent re assortment and the generation of new combinations of the genetic factors of a diploid genome into a haploid genome of the gametophytes. The genotype of one progeny plant is the combination of genotypes of one male and one female gamete, which fused to form a new sporophyte. Meiosis can therefore be considered to be a pivotal process during the life cycle of any living organism to create genetic variability.

This variability is used to obtain desired plants with new properties. Often the combination of the different properties of the two parents in a hybrid is more advantageous than a homozygous (parental) plant. The production of such hybrids is however rather complicated. In the case of F1 hybrids, several putative parental lines are first made homozygous, e.g. by many generations of inbreeding and selection and subsequently they are crossed in various combinations to study their combining ability. The best combinations and their respective parental lines are subsequently retained and give rise to a commercial F1 variety.

However, the normal way of obtaining desirable hybrids is rather time consuming since homozygous parental lines have to be produced first and the desired combination of two of these homozygous parental lines has then to be selected. This process requires several generations.

Also in the case of animals, like for example farm animals, such as cattle, pigs, fish, such as salmon, and fungi, such as mushrooms, hybrids may be desirable but since animals take an even longer time to become sexually mature and reproduce it takes even longer to produce homozygous lines and select for the best combination of those to produce a hybrid. Examples of animals for which the invention may be useful include rainbow trout and aquarium fish such as zebrafish.

SUMMARY OF THE INVENTION

It is therefore a first object of the present invention to provide an alternative method for providing homozygous parental lines for the production of hybrids.

It is a second object of the invention to use this method to provide even more flexibility in combining desirable parental traits in heterozygous off spring.

In this application sometimes reference is made solely to plants. However, in such cases one could also read fungi or animals, except where it is clear from the context that only plants can be intended.

According to the invention it was surprisingly found that the reverse of traditional breeding is possible, i.e. starting with the heterozygous plant to produce homozygous parental lines. The homozygous parental lines can reconstitute the original heterozygous plant or animal by crossing, if desired even in a large quantity. An individual heterozygous plant can surprisingly be converted in a heterozygous (F1-hybrid) variety without the necessity of vegetative propagation but as the result of the cross of 2 homozygous lines derived from the original selected plant.

The present invention thus relates to a method for efficiently producing homozygous organisms from a heterozygous non-human starting organism, comprising:

a) providing a heterozygous starting organism;

b) allowing the starting organism to produce haploid cells;

c) creating homozygous organisms from the haploid cells thus obtained; and d) selecting the organisms having the desired set of chromosomes;

characterized in that during production of the haploid cells essentially no recombination occurs in order to obtain a limited number of genetically different haploid cells.

In a preferred embodiment of the invention recombination is at least partially prevented or suppressed in contrast to situations in which the starting organism is selected for its inability to have recombination upon the formation of haploid cells.

The method can be used for plants, fungi and animals except humans.

By preventing or suppressing recombination the normal variation that arises in every natural cross can be limited or even avoided. As a result thereof, the number of haploid cells having different sets of chromosomes is considerably reduced. Because of this, the cell or organism regenerated therefrom with the desired set of chromosomes can be quite easily identified.

When the chromosome set of such cell or organism regenerated therefrom is doubled a homozygous cell or organism arises. Such organism can then be used in crosses with another homozygous organism produced in the same way from the same donor organism to produce a hybrid organism.

The "desired set of chromosomes" can be one of a number of variants. In case the original starting hybrid is to be produced the two homozygous organisms produced according to the invention should together have the exact set of chromosomes of the starting organism. This is achieved when both parents have the same set of chromosomes as the gametes that formed the hybrid. However, it is also possible that the new maternal line has only some of the chromosomes of the original maternal gamete and the others of the original paternal gamete ("chromosome substitution"). In that case the other parent should again have the complement thereof if the production of the same hybrid is desired.

It is however also possible to combine the new line which has one or more but not all of the chromosomes of the original parent with a different parent in plant breeding. The new homozygous lines as such can thus be a newly desired end product. This applies to lines having the original parental chromosome composition as well as to lines having a new combination of chromosomes.

Recombination can be prevented or suppressed by various means, in particular through dominant transgenic approaches, dominant negative mutation or treatment with a chemical.

In a first embodiment, the prevention or suppression of recombination is achieved by interfering with one or more target genes involved in recombination. The target genes can be involved in double strand breaks, chromosome pairing, crossing-over and separation of sister chromatids.

Target genes (GenBank accession nos.) involved in the formation of double strand breaks are SPO11 (J02987.1), MER1 (M31304.1), MER2 (M38340.1), MRE2 (D11461.1), MEI4 (M84765.1), REC102 (M74045.1), REC104 (Z15007.1), REC114 (Z14315.1), MEK1/MRE4 (X63112.1), RED1 (X16183.1), HOP1 (J04877.1), RAD50 (X14814.1), MRE11 (U60829.1), XRS2 (L22856.1), identified in yeast, or their functional homologues from other species.

Target genes (GenBank accession nos.) involved in chromosome pairing and/or strand exchange are RAD54/TID1 (M63232.1), DMC1 (M87549.1), MND1 (protein accession NP_011332.1), SAE2 (U49447.1), SAE3 (U82546.1), RED1 (X16183.1), HOP1 (J04877.1), HOP2 (AF078740.1), REC8 (AJ223299.1), MER1 (M31304.1), MRE2 (D11461.1), ZIP1 (L06487.1), ZIP2 (protein accession: NP_011265.1), MEI5 (L03182.1), RAD51 (X64270.1), RAD52 (M10249.1), RAD55 (U01144.1), RAD57 (M65061.1), RPA (M60262.1), SMC3 (Y14278.1), SCC1 (Y14280.1), MSH2 (M84170.1), MSH3 (M96250.1), MSH6 (AL031545), PMS1 (M29688.1), MER3 (P51979), DDC1 (protein accession NP_015130.1), MMS4 (U14000.1), identified in yeast, SOLODANCERS (AJ457977.1), KU70 (AF283759.1), KU80 (AF283758.1) identified in *Arabidopsis thaliana*, HIM6 (AY095296.1), CDS1 (Y60A3A.12), CDS2 (T08D2.7), identified in *Caenorhabditis elegans*, SCP3 (X75785.10), identified in *Rattus norvegicus*, MEI218 (U35631.2), identified in *Drosophila melongaster*, or their functional homologues from other species.

After recombination complexes are formed (double holliday junctions) these are processed to either crossing-over events or non-crossing-over events (called gene conversion). Most recombination complexes lead to gene conversion, whereas only a few crossing-over events lead to recombination. Interfering in this last phase of meiosis to have more gene conversion leads to a lower recombination frequency, and can be achieved via target genes (GenBank accession nos.) selected from the group consisting of SGS1 (U22341.1), MSH4 (U13999.1), MSH5 (L42517.1), ZIP1 (L06487.1), ZIP2 (protein accession: NP_011265.1), MLH1 (U07187.1), MEC1 (U31109.1), MLH3 (protein accession NP_015161.1) from yeast, or their functional homologues from other species.

In the present invention use can be made of the above genes originating from the organism in which they were first identified or the corresponding genes in other organisms, such as plants, that have the same name and/or the same function (called herein "their functional homologues from other species"). Functional homologues of the above genes that are involved in meiotic recombination constitute potential targets for modification in plants or other species in which meiotic recombination is to be suppressed. The fact that the products they encode perform the same or a similar biological function does not necessarily mean that the genes have a significantly higher level of identity than genes which are not functional homologous.

According to the present invention a (candidate) target gene is defined as a gene residing within the genome of an organism which upon quantitative and/or qualitative modification of its expression results in a modified meiotic process within said organism which is characterized by the formation of functional, haploid spores that contain a full set of chromosomes but which have not been subjected to meiotic recombination or which have been subjected to a reduced frequency of meiotic recombination as compared to the situation in which said gene is not modified.

Different genes and their functional homologues, which can but not necessarily need to be homologous, qualify as (candidate) target genes. The only common denominator of target genes of the invention is the fact that upon their modification meiotic recombination is suppressed.

Once a target gene has been selected for modification this can be achieved in various manners.

In a first embodiment interfering with the target gene consists of preventing transcription thereof. This can be achieved by means of RNA oligonucleotides, DNA oligonucleotides or RNAi molecules directed against the target gene promoter.

Alternatively, transcription is prevented by means of the expression of a negatively acting transcription factor acting on the target gene promoter. Such negatively acting transcription factor can be natural or artificial. Artificial negatively acting transcription factors can be employed by the overexpression of an engineered polydactyl zinc-finger transcription factor coupled to a general transcription repressor.

According to a further embodiment, the interfering with the target gene consists of destabilizing the target gene mRNA, in particular by means of nucleic acid molecules that are complementary to the target gene mRNA selected from the group consisting of antisense RNA, RNAi molecules, Virus Induced Gene Silencing (VIGS) molecules, co-suppressor molecules, RNA oligonucleotides or DNA oligonucleotides.

In another embodiment the interfering with the target gene consists of inhibiting the target gene expression product. This can be achieved by means of the expression product(s) of one or more dominant negative nucleic acid constructs, overexpression of one or more suppressors which interact with the target gene product, or by means of one or more chemical compounds.

Furthermore, interfering with the target gene can consist of the introduction of one or more mutations into the target gene leading to perturbation of its biological function. The one or more mutations can be introduced randomly by means of one or more chemical compounds and/or physical means and/or insertion of genetic elements. Suitable chemical compounds are ethyl methanesulfonate, nitrosomethylurea, hydroxylamine, proflavine, N-methyl-N-nitrosoguanidine, N-ethyl-N-nitrosourea, N-methyl-N-nitro-nitrosoguanidine, diethyl sulfate, ethylene imine, sodium azide, formaline, urethane, phenol and ethylene oxide. Physical means that can be used comprise UV-irradiation, fast-neutron exposure, X-rays and gamma irradiation. The genetic element is a transposon, T-DNA, or retroviral element.

Mutations may also be introduced specifically by means of homologous recombination or oligonucleotide-based mutation induction.

According to a further embodiment of the invention, the prevention or suppression of recombination is achieved by a chemical compound preventing the spindle from being formed or by a chemical compound inducing aneuploidy.

After the starting plant has been treated such that recombination is prevented or suppressed before or while haploid cells are being formed, these cells are isolated and used for regeneration of a complete plant. Such plant is haploid and can become diploid either spontaneously or through other means, such as treatment with colchicine.

Haploid cells can be derived from germ line cells such as spore mother cells or somatic cells that have become haploid by means of a natural or induced process.

Once the haploid plant is diploidized it is homozygous for all chromosomes and it can be used for various purposes.

It is possible to derive the chromosome composition of the original parents (so-called "original parental line rescue") of the hybrid that is the subject of reverse breeding by molecular analysis of either the seed coat or the endosperm. The endosperm contains a double maternal genetic dosage. A quantitative assay can be used to determine which chromosomes are derived from the mother (twice the dosage) and which from the father (once the dosage). The seed coat is maternal and represents the chromosome composition that originates from the mother.

The production of F1 hybrids can now be done in completely the reverse order. Instead of selecting so-called original parental lines, and testing suitable combinations, a heterozygous plant with an expected suitable combination of allelic forms of genes is selected, and corresponding parental lines that could be used for the production of F1 hybrid seeds of the same plant are derived from this plant. This process is herein called "reverse breeding".

Importantly, reverse breeding technology allows a significant flexibility in the plant breeding process because in addition to the efficient reproduction of the exact starting genotype, for each individual chromosome a choice can be made to retrieve it either in a homozygous maternal, homozygous paternal or heterozygous form as will be explained hereinbelow.

Effectively, reverse breeding can be performed by preventing meiotic recombination in combination with efficiency enhancing methods for generating the parental lines, which in a preferred embodiment concerns the production of doubled haploid plants and/or molecular genotyping technologies. Other methods are second generation restitution and self pollination. In the latter case, plants in which recombination has been prevented or suppressed are selfed to produce selfing seed. Molecular genotyping techniques are then used to identify the homozygous plants in the S1.

BRIEF DESCRIPTION OF THE DRAWINGS

FIG. 1 is a partial nucleotide sequence of BoDMC1 (SEQ ID NO: 1);

FIG. 2 is a partial nucleotide sequence of BcDMC1 (SEQ ID NO: 2);

FIG. 3 is a partial nucleotide sequence of LeDMC1 (SEQ ID NO: 3);

FIG. 4 is a partial nucleotide sequence of SmDMC1 (SEQ ID NO: 4);

FIG. 5 is a partial nucleotide sequence of NtDMC1 (SEQ ID NO: 5);

FIG. 6 is a partial nucleotide sequence of BoSPO11 (SEQ ID NO: 6);

FIG. 7 is a partial nucleotide sequence of BcSPO11 (SEQ ID NO: 7);

FIG. 8 is a partial nucleotide sequence of AtMSH5 (SEQ ID NO: 8);

FIG. 9 is a result of a BLAST X analysis of the AtMSH5 partial nucleotide sequence (query) (SEQ ID NO: 27) showing the level of identity of the translated AtMSH5 sequence with known MSH5 orthologues (Sbjct) from *Saccharomyces cerevisiae* (SEQ ID NO:28), *Homo sapiens*, (SEQ ID NO: 29), *Mus musculus* and (SEQ ID NO: 30) *Caenorhabditis elegans* (SEQ ID NO: 31);

FIG. 13 is a partial nucleotide sequence of BoMSH5 (SEQ ID NO: 17);

FIG. 14 is a partial nucleotide sequence of LeMSH5 (SEQ ID NO: 18);

FIG. 15 is a partial nucleotide sequence of SmMSH5 (SEQ ID NO: 19); and

FIG. 16 is a partial nucleotide sequence of NtMSH5 (SEQ ID NO: 20).

DETAILED DESCRIPTION OF THE INVENTION

Figure 10:
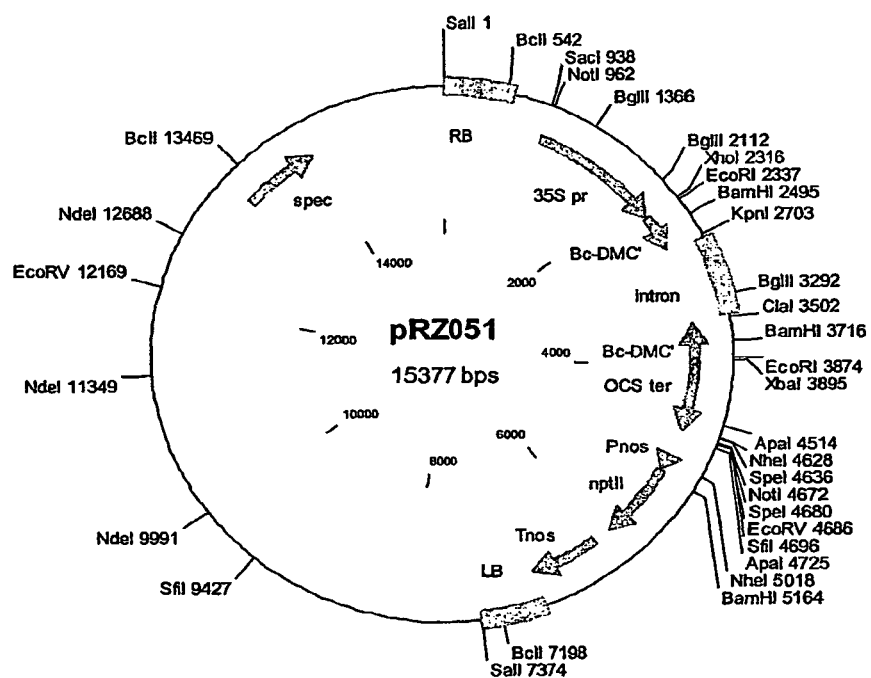
FIG. 10 is a Map of pRZ51. RB=right border, LB=left border, spec=spectinomycin/streptomycin resistance, 35S pr=CaMV 35S promoter, Bc-DMC=BcDMC1, OCS-ter=octopine synthase promoter, Pnos=nopaline synthase promoter, NPTII=neomycin phosphotransferase II, Tnos=nopaline synthase polyadenylation signal.

The invention thus relates to the prevention or suppression of recombination in a process for the production of haploid cells and to the production of homozygous lines from these cells.

Haploid cells can be the result of meiosis or are derived from somatic cells. In the latter case chemical compounds can be used to haploidize the cells. Alternatively, reductional grouping is induced. In reductional grouping the chromosomes are distributed over the daughter cells without the help of the spindle fibres and without DNA replication. After cell division haploid cells are formed. Reductional grouping can be induced by treating (root) meristem or protoplasts with a chemical, such as caffeine or by neutralizing the genetic target of the chemical with a gene construct. Expression of the construct must be inducible because constitutive expression of the neutralizing construct would be lethal.

According to the invention haploid cells are however preferably derived from a meiotic process. The process of meiosis forms the pivotal event in the life cycle of living organisms at which genetic variation is created. Moreover it marks the transition between the diploid, sporophytic and the haploid, gametophytic generation which alternate during the life cycle of a plant. The specialized cell in the female reproductive organ which enters meiosis, which is called megaspore mother cell, is embedded in the differentiated ovule inside the ovary. During ovule formation, a number of mitotic events lead to the differentiation of a single megaspore mother cell per ovule out of a few archesporial cells which develop from hypodermal cells.

Within the male reproductive tissues (the anthers), a similar process leads to the formation of microspore mother cells although the archesporial cells undergo several rounds of mitosis before differentiating into microspore mother cells. As a consequence each anther contains a large number of microspore mother cells.

A few mutants of maize and *Arabidopsis* have been identified which are disturbed in the early functions of these differentiation processes. The macl (multiple archesporial cells) mutant of maize is disturbed in a gene that plays a role in the withdrawal of hypodermal cells from the mitotic into the meiotic pathway (Sheridan, W. F. et al (1999) Genetics 153, 933-941). The spl (sporocyteless) mutant in *Arabidopsis* is disturbed in the differentiation of mega- and microspore mother cells from archesporial cells (Yang, W-C, et al (1999) Genes Dev. 13, 2108-2117).

The macro- and microspore mother cells, collectively called meiocytes, undergo meiosis, which results in the formation of four haploid spores per meiocyte. Three of the four female spores or megaspores degenerate through callose deposition. The surviving megaspore differentiates after 3 nuclear divisions and subsequent cellularisation into the female gametophyte or embryosac.

The four male spores or microspores usually remain together and form a so-called tetrad structure. Upon differentiation of the male gametophytes from the microspores, the tetrad structure is dissolved and the male gametophytes or pollen behave as loose entities.

Although there are significant differences in the cellular processes leading to the formation of female and male meiocytes as well as the differentiation of the macro- and microspores into an embryosac and pollen, respectively, the cytological events which occur during female and male meiosis are very similar suggesting the involvement of common gene products.

However, this does not necessarily mean that each of the events during female and male meiosis is controlled by identical genetic loci. For example, in *Arabidopsis* the ASK1 gene is specifically involved in male meiosis (Yang, M. et al (1999) Proc. Natl. Acad. Sci. USA 96, 11416-11421) whereas SWI1 (Motamayor, J. C. (2000) Sex. Plant Reprod. 12, 209-218), DYAD (Siddiqi, I. et al (2000) Development 127, 197-207) and ANTIKEVORKIAN (Yang, W-C. and Sundaresan (2000) Curr. Opin. Plant Biol. 3, 53-57) are specific for female meiosis.

During meiosis a number of cytological phases are distinguished and for each phase a number of mutants has been described in plants.

During the initial phase called meiotic Prophase a number of stages are discerned. During the initial stage called Leptotene, the individual chromosomes which have been replicated and which consist of two sister chromatids start to condense and become shorter and thicker. Simultaneously, the nuclear envelope starts to disintegrate and the homologous chromosomes start to associate. The next stage is called Zygotene in which the chromosomes are fully condensed and in which the homologous chromosomes align and start to form the so-called synaptonemal complex (SC). The dif1/syn1 mutant of *Arabidopsis* is impaired in the formation of the SC (Bhatt, A. M. et al (1999) Plant J. 19, 463-472; Bai, X. et al (1999) Plant Cell 11, 417-430). The DIF1/SYN1 gene products are homologous to the yeast cohesin REC8/RAD21 which function in synapsis and recombination. At Pachytene the formation of the SC is completed for all chromosomes. At this stage meiotic recombination occurs which is initiated by the formation of double-stranded breaks followed by chromatid exchange between homologous chromosomes. The physical links that are established between the non-sister chromatids and which persist even in the absence of the synaptonemal complex are called chiasmata. During Diplotene and Diakinesis the chromosomes fully condense, the nuclear envelope has disappeared and the spindle fibers have been formed. Subsequently during Metaphase I, the pairs of homologous chromosomes are located in the equatorial plane of the cell. Then, during Anaphase I, the homologous chromosomes, each consisting of two sister chromatids which may have undergone a number of recombination events and are held together by a centromere, move towards the opposite cellular poles. During Telophase I, the polar movement is completed, the spindle disappears and the cell starts to divide.

Subsequently, these cells enter Prophase II that is characterized by the alignment of the condensed chromosomes on the equatorial plane. A spindle complex is being formed. During Metaphase II the chromosomes are fully aligned at the equatorial plane and the spindle complex is completed. During the next phase, called Anaphase II, the centromeres divide and the sister chromatids move towards opposite poles. In Telophase II this movement process is completed, the spindle complex starts disappearing and cell division initiates. Subsequently, the chromosomes resume their Interphase appearance characterized by uncoiled chromosomes located inside the nuclear envelope.

The end product of meiosis II is a set of four genetically distinct haploid cells, which can undergo mitosis to develop into gametophytes. The gametophytes produce the gametes, which upon fusion leads to the formation of a zygote, which develops, into an embryo that can grow out into the next generation sporophyte.

The genetic variation, which occurs in the sporophyte, is determined by the genotypes of the female and male gametes that fused upon the formation of the zygote. Therefore this genetic variation is created during the formation of the female and male spores during meiosis which leads to genetic re-assortment of the original parental chromosomes as well as chromosomal regions due to recombination events.

Meiosis and meiotic recombination are intricate processes which have been studied to different degrees, at different levels in different organisms. The molecular mechanism through which meiotic recombination occurs is not yet entirely clear. One model is the double strand break (DSB) repair model according to which meiotic recombination is initiated by the formation of double strand breaks (DSBs) in one of the two interacting non-sister chromatids. The formation of the DSBs is initiated by a protein. This protein has been identified in yeast and is called therein SPO11 protein. Homologues of the SPO11 protein of yeast were found in Schizosaccharomyces pombe named REC12, Arabidopsis, Drosophila, Caenorhabditis, mouse and man. Arabidopsis is the only eukaryote known so far to contain 3 paralogous SPO11 genes. The homology, which resides within the SPO11 proteins, is confined to five conserved motifs.

Next to the DSB formation, an exonuclease activity evoked by a protein complex in which MRE11, RAD50 and XRS2/NBS1 of yeast participate, resects the 5'-ends of the break in the 3'-direction, which results in 2 3'-OH single stranded tails. One of these tails invades the double stranded DNA of the paired chromatid through base pairing with the complementary strand. Strand invasion involves RecA-like proteins, of which DMC1 is specific for meiotic recombination. Through a DNA repair mechanism a bimolecular intermediate containing two Holliday junctions is formed which involves the proteins MSH4, MSH5 and MLH1 in yeast. A Holliday junction resolution system, containing resolvases, can result in gene conversion or crossover.

A large number of proteins has been identified which are involved in this process which can either be specific for meiotic recombination or can be involved in mitotic DSB and mismatch repair as well. Homologues of many of these proteins are being identified in plant systems like Arabidopsis thaliana and the corresponding genes have been cloned. The plant homologues of the SPO11 protien have been identified in Arabidopsis thaliana and are named AtSPO11 and AtDMC1 (Couteau, F. et al (1999) Plant Cell 11, 1623-1634). They are involved in bivalent stabilization and chromosomal segregation.

According to the invention recombination in the starting organism is to be prevented or suppressed. This prevention or suppression can be attained at various levels of the recombination event. No recombination can occur when no double strand breaks are produced, when the crossing-over is impaired and when the chromosomes cannot pair. Various genes are involved in all these events. Impairing the function of one or more of these genes leads to prevention (on/off) or suppression (lower level) of recombination. For the purpose of this application, such genes are called "(candidate) target genes".

Interfering with the function of these genes can be achieved through a number of approaches which are either based on homology dependent gene silencing mechanisms such as co-suppression, antisense downregulation or RNA interference or which are based on expression of proteins which interfere with the functionality of the target protein. The latter method is for example downregulation through a dominant negative approach.

In case use is made of a homology dependent gene silencing approach, the gene construct which is used to achieve the silencing effect should contain a DNA fragment which has a percentage of identity at the nucleotide level with a region of the target gene which is sufficient to downregulate this target gene to the extent that it results in the formation of viable, haploid spores that contain a full set of chromosomes which have not been subjected to meiotic recombination or which have been subjected to a reduced frequency of meiotic recombination as compared to the situation in which the target genes are not downregulated. This result can either be achieved after selecting a random fragment of the gene or by selecting those segments of the gene as silencing fragment which encode the conserved domains of the encoded protein.

In case there is not a sufficient percentage of identity between the silencing DNA fragment and a specific region of the functional homologue of the gene which resides in the genome of a given crop species to achieve a sufficient level of downregulation, a fragment of the functional homologue of the gene itself can be used to achieve downregulation of this functional homologue within the crop species from which it has been derived.

Functional homologues, which reside in other crop species, can be down-regulated using the silencing DNA fragment if there is sufficient homology.

In a preferred embodiment of the invention, modification of the target genes is achieved by genetic engineering of the crop species. The nature of the modification of the target gene can either be downregulation, which means that the expression of the target gene is reduced or ectopic (over)expression, which means that the expression of the target gene is increased, and optionally taking place at a time different from the natural expression. In the case of ectopic (over)expression the target gene involved in recombination has a repressor function.

In order to downregulate a target gene, various methods can be used that are based on homology with the target gene.

In a particular embodiment the downregulation of the target gene is achieved through a method referred to as antisense technology. In this method a gene is expressed in its reversed orientation with respect to a transcriptional promoter. This can be achieved by introduction of a gene construct into the genome of a plant in which the segment of a gene, which is normally expressed as RNA, is reversed in its orientation relative to a transcriptional promoter. Usually such a construct is referred to as antisense construct. Upon expression of the antisense construct in a plant, the plant produces RNA molecules that are synthesised using the coding strand of the gene construct as a template and therefore are complementary to the coding strand. Usually this type of RNA is referred to as antisense RNA. The result of the expression of an antisense construct is that the gene or genes which reside in the same plant and which upon expression leads to the synthesis of RNA complementary to the antisense RNA are effectively silenced.

In another embodiment the downregulation of the target gene is achieved through a method referred to as cosuppression technology. In this method a gene is expressed in the sense orientation with respect to a transcriptional promoter. This can be achieved by introduction of a gene construct into the genome of a plant in which the segment of a gene which is normally expressed as RNA has the same orientation relative to a transcriptional promoter as in a native gene. Usually such construct is referred to as cosuppression or sense cosuppression construct.

Upon expression of the cosuppression construct in a plant, the plant produces RNA molecules that are synthesized using the non-coding strand of the gene construct as a template and therefore are complementary to the non-coding strand. Usually this type of RNA is referred to as cosuppression RNA. The result of the expression of a cosuppression construct is that the gene or genes which reside in the same plant and which upon expression leads to the synthesis of homologous RNA are effectively silenced.

In yet another embodiment the downregulation of the target gene is achieved through a method referred to as RNA interference (RNAi). RNAi is a general term which refers to a phenomenon in which double stranded RNA (dsRNA) molecules very effectively mediate gene silencing of genes with homology to the dsRNA. Silencing of an endogenous gene triggered by dsRNA is the result of post transcriptional gene silencing which is a phenomenon in which an RNA transcript is synthesized and rapidly and specifically degraded. RNAi has initially been demonstrated to operate in *Caenorhabditis elegans* (Fire, A. et al (1998) Nature 391, 806-811). RNAi has also been demonstrated to be effective in other organisms including plants (Chuang, C-F. and Meyerowitz, E. M. (2000) Proc. Natl. Acad. Sci. USA 97, 4985-4990). Transgenes designed to express RNA which is self-complementary and thereby is able to form duplexes or hairpin RNAs were shown to be highly effective in triggering virus resistance and gene silencing (Smith, N. A. et al (2000) Nature 407, 319-320).

In yet another embodiment of the invention suppression of the target gene may be achieved through specific transcriptional silencing of the target gene via the promoter. This may be achieved through expression of an RNAi construct which results in the synthesis of double stranded RNA molecules of which the nucleotide sequence is identical to a part of the promoter region of the target gene. The promoter region of a gene is located upstream (with respect to the trancriptional direction) of the position at which transcription of the gene is initiated.

In yet another embodiment of the invention, suppression of the target gene may be achieved through a methodology generally referred to as Virus Induced Gene Silencing or VIGS (Ratcliff et al (2001) Plant J. 25, 237-245). In such an approach effective and specific gene silencing is achieved by infection of a plant with a plant virus carrying an insert which is homologous to the gene which needs to be silenced. The advantage of the VIGS systems is that there is no need to develop a plant transformation protocol for the plant species for which silencing of a target gene is pursued.

In all these embodiments, the silencing construct (antisense RNA, co-suppression, RNAi or hairpin construct or VIGS vector) preferably contains a DNA fragment that is identical to the target sequence (gene or promoter) that needs to be silenced. However, the percentage of identity may also range between 50 and 100%, preferably between 60 and 100%, more preferably between 70 and 100%, even more preferably between 80 and 100%, most preferably between 90 and 100%.

The length of the DNA fragment in the silencing construct should be at least 20 nucleotides but can also be longer to a maximum of the full-length target sequence which needs to be silenced.

The transcriptional promoter which is used to synthesize the silencing molecule can be a constitutive promoter or a promoter which is developmentally regulated. The promoter may also be inducible for example by a chemical compound.

Preferably, but not necessarily the expression of the silencing construct and the target gene that needs to be silenced coincides. This does not apply to the silencing via the promoter of a gene because this approach is directed to avoiding transcription so that no transcript is formed. The other techniques neutralize the transcription product after it is produced.

In yet another embodiment of the invention suppression of the target gene may be achieved through specific silencing of the target gene by introduction of RNA oligonucleotides (Tijsterman et al (2002) Science 295, 694-697). This may be achieved through chemical synthesis of RNA oligonucleotides of which the nucleotide sequence is identical to a part of the promoter region or transcribed region of a target gene and introduction of the silencing oligonucleotides into the cell. The advantage of this specific embodiment of the invention is that there is no need to adopt a transgenic route in achieving reverse breeding for a specific target crop.

Like in the other embodiments that use homology dependent gene silencing mechanisms, the RNA oligonucleotide which is used to silence a target gene preferably has a nucleotide sequence which is identical to a part of the promoter or transcribed region of the target gene that needs to be silenced. However the percentage of identity may also range between 50 and 100%, preferably between 70 and 100%, even more preferably between 80 and 100%, most preferably between 90 and 100%. The single stranded RNA oligonucleotide may be identical to either the sense or antisense strand of the DNA of the promoter or transcribed region of a target gene. Alternatively, instead of using single stranded RNA oligonucleotides, single stranded DNA oligonucleotides may be used of which the nucleotide sequence is designed as if it would be an RNA oligonucleotide. Moreover both double stranded RNA as well as DNA oligonucleotides may be used.

The oligonucleotides can be introduced into plants or plant cells by methods well known to the person skilled in the art. These may include but are not limited to polyethylene mediated uptake in protoplasts or particle gun mediated uptake in plants or plant parts.

When suppression of target genes is pursued through a homology based method like RNA interference, VIGS, oligonucleotides or others it is preferred to carry out a search for sequences that are homologous to the target sequence and that reside within the genome of the species to be subjected to recombination suppression or prevention. "Homologous" is intended to mean here "having a level of identity with the nucleic acid fragment which is used to effectuate the homology based suppression of the target gene that leads to suppression of the sequences outside the target gene". In case such sequences are found it may be desirable to use another fragment of the target gene for design of the silencing sequence in order to avoid interference with other parts of the genome.

In another embodiment suppression of the activity of the target gene may be achieved through overexpression of a dominant negative construct, a process well known to the person skilled in the art. In such approach a gene encoding a protein or modified protein is overexpressed in the crop species in which a target gene needs to be suppressed according to the present invention. The gene which encodes such a protein usually is referred to a dominant negative gene as the effect of (over)expression is inherited as a dominant genetic factor and it is causing a specific loss of function. The transcriptional promoter which is used to synthesize the dominant negative construct can be a constitutive promoter or a promoter which is developmentally regulated. The promoter of the dominant negative construct may also be inducible for example by a chemical compound.

The expression of the dominant negative construct and the target gene that needs to be suppressed should be spatially and temporarily regulated such that the target gene is effectively suppressed. Preferably but not necessarily, the promoter of the dominant negative construct and the target gene are regulated such that they are expressed in essentially the same part of the plant at essentially the same time.

According to yet another embodiment of the invention suppression of target genes is achieved through overexpression of a natural suppressor of the target gene. Such a suppressor may be a negatively acting transcription factor that acts on the promoter of target genes or a protein which interacts with the gene product of the target genes in such a way that this gene product can not fulfil its natural function. The expression of a suppressor construct and the target gene that needs to be suppressed should be spatially and temporarily regulated such that the target gene is effectively suppressed. Preferably but not necessarily, the promoter of the suppresser construct and the target gene are regulated in an highly similar manner in terms of their spatial and temporal activity, i.e. they are expressed essentially at the same time in the same part of the plant. The promoter of the suppressor construct may also be inducible for example by a chemical compound.

In a specific embodiment of the present invention, a silencing construct is used that modifies a target gene which specifically results in suppression of either female or male meiotic recombination. This can be achieved by interfering with the activity of a gene product that is specifically active in either female or male meiotic recombination. Alternatively, this can be achieved by using a silencing construct that is specifically active during female or male meiosis. The latter kind of construct can either interfere with a target gene that is specifically involved in female or male meiotic recombination or a target gene that is involved in both female and male meiotic recombination.

This specific embodiment of the invention has practical utility when the suppression of meiotic recombination leads to a reduction of the quality of the spores, such as a reduced number of functional haploid spores. Plants that are suppressed in female meiotic recombination but not in male meiotic recombination can be used as efficient pollinators to produce new hybrids and vice versa, the plants that are suppressed in male meiotic recombination can be used as efficient female lines during the production of new hybrids.

In case transgenic approaches are used for preventing or suppressing recombination, so-called chimeric gene constructs can be made using standard molecular cloning techniques well known to the person skilled in the art and which can for example be found in Sambrook, J and Russell, D. W.: Molecular cloning, a laboratory manual (third edition), Cold Spring Harbor Laboratory Press, Cold Spring Harbor, N.Y. Such constructs are "chimeric" in the sense that they consist of various DNA fragments originating from various sources.

The chimeric constructs which are made to modify the activity, in particular transcription or translation, but also transcript processing, protein modification, protein targeting, complex formation and activity, of the target genes usually comprise a promoter sequence and a polyadenylation signal sequence that are operably linked to the DNA fragment that is being used to achieve suppression of meiotic recombination such that a functional chimeric gene construct is produced.

In order to transfer a chimeric gene construct into the genome of a plant, transformation vectors are prepared using standard molecular cloning techniques well known to the person skilled in the art and which can for example be found in Sambrook, J and Russell, D. W.: Molecular cloning, a laboratory manual (third edition), Cold Spring Harbor Laboratory Press, Cold Spring Harbor, N.Y.

Promoter sequences which can be used according to the present invention include but are not limited to constitutive promoters like the CaMV 35S promoter (Odell, J. T. et al (1985), Nature 313, 810-812), the *Arabidopsis* Actin 2 promoter (An, Y. Q. (1996) Plant J. 10, 107-121), the maize Ubiquitine 1 promoter (Drakakaki, G. et al (2000) Transgenic Res. 9, 445-452), the rice Actin 1 promoter (McElroy, D. et al (1990) Plant Cell 2, 163-171) and the *Arabidopsis* Farnesyl diphosphate synthase 1S promoter (Cunillera, N. et al (2000) Plant Molec. Biol. 44, 474-485) or developmentally regulated promoters like the *Arabidopsis* Actin 11 promoter (Huang, S. et al (1997) Plant Molec. Biol. 33, 125-139), the *Arabidopsis* DMC1 promoter (Klimyuk, V. I. and Jones, J. D. (1997) Plant J. 11, 1-14) or the *Arabidopsis* SPO11-1 promoter (Grelon, M. (2001) EMBO J. 3, 589-600).

Other developmentally regulated promoters may be derived from the target gene itself.

Inducible promoter systems which can be used are the ethanol inducible gene switch system (Caddick, M. X. et al (1998) Nat. Biotechnol. 16, 177-180) and the glucocorticoid inducible system (Schena, M. et al (1991) Porc. Natl. Acad. Sci. USA 88, 10421-10425).

Polyadenylation sequences which may be used in constructs of the present invention include but are not limited to the *Agrobacterium* octopine synthase polyadenylation signal (MacDonald et al (1991) Nucleic Acids. Res. 19, 5575-5581), the pea ribulose bisphophate carboxylase polyadenylation signal (Hunt, A. G. and MacDonald M. H. (1989) Plant Molec. Biol. 13, 125-138).

According to a further aspect of the invention prevention or suppression of recombination can be achieved by randomly inducing changes in the genome of the organism and selecting those mutants that have acquired a change in the target gene that leads to the desired suppression or prevention of recombination.

In a preferred embodiment of this aspect of the invention, modification of the target genes is achieved by mutagenesis of the crop species. Random mutations can be introduced into a plant genome by chemical means like treatment with ethyl methanesulfonate or nitrosomethylurea, by Morphogenics technology (BioWorld Today (2000), 11(108), 1-2) or physical means like UV-irradiation, fast-neutron exposure or insertional mutagenesis using transposons or T-DNAs. Specific mutations can be introduced into a plant genome through homologous recombination (Paszkowski, J. et al (1988) EMBO J. 7, 4021-4026; Mengiste, T. and Paszkowski, J. (1999) Biol. Chem. 380, 749-758); Vergunst, A. C. and Hooykaas, P. J. J. (1999) Crit. Rev. Plant Sci. 18, 1-31) or oligonucleotide-based mutation induction (Oh, T. J. and May, G. D. (2001) Curr. Opin. Biotechnol. 12, 169-172).

Plants in which the target gene is mutated can be readily identified by screening methods like TILLING (Colbert, T. (2001) Plant Physiol. 126, 480-484) or DELETAGENE (Li, X. et al (2001), 12th International conference on *Arabidopsis* research (Abstract nr. 2)) which allow to detect aberrations residing within the target gene.

Preferably a mutant is selected in which the modification of the target gene is conditional, which means that the mutant phenotype only becomes manifest upon exposure of the plant to a specific environmental condition like a specific temperature. This allows to induce the modification only by exposing the plant to the specific environment. Under the conditions in which the modification is not manifest, the mutant can be used for normal crossing and seed production.

In yet another preferred embodiment of the invention, modification of the target genes is achieved by treatment of the crop species with specific chemical compounds which through interference with the products of the target genes result in inhibition or reduction of meiotic recombination. An example of such chemical compound is etoposide which through inhibition of the topoisomerase-II results in inhibition of meiotic recombination (Russell, L. B. et al (2000) Mutat. Res. 464, 201-212).

In yet another preferred embodiment of the invention, aneuploidy can be induced chemically by treatment of pre-meiotic cells with certain chemical compounds. This may be done by chemical treatment of floral buds containing these pre-meiotic cells by submergence or spraying. Such method may effectively be applied to modify meiotic recombination as has been shown in patent application WO0054574. The mechanism by which a chemical compounds induces aneuploidy is not always clear but there is experimental evidence that aneuploidy can occur through interference with the spindle mechanism during mitosis and meiosis, fragmoplast function and chiasmata formation. The chemical that may be applied to induce aneuploidy is selected from but not limited to chemicals such as etoposide, podophyllin, benomyl, maleic hydrazide, atrazine, butachlor, APM, griseofulvin, vinblastin-sulphate, diazepam, colchicine, cadmium chloride, econazole, pyrimethamine, thiabendazole, thimerozal or nocodazole. Further details on aneuploidy inducing chemical compounds and their mode of action as well their effective concentration can be found in C. B. S. R. Sharma (1990) Mutagenesis 5, 105-125 and references therein as well as in Sandhu et al (1991) Mutagenesis 6, 369-373.

After treatment of floral buds with the chemical compound which induces aneuploidy, spores can be isolated from the treated buds which can be induced to regenerate. Homozygous plants may be obtained through doubling of the chromosome number e.g. through treatment with colchicine in case spontaneous doubling has not been taken place already. The population of double haploid plants obtained through this method can be analysed for the presence of a full complement of chromosomes by molecular detection of marker alleles known to reside on a specific chromosome.

Gynogenesis is particularly suitable for applying reverse breeding effectuated by chemical treatment. By using such method the specific chemical may be applied through the tissue culture medium used to apply gynogenesis. It may also be possible to treat the sterilised ovaries directly with the chemical compound that prevents meiotic recombination. The reason for this particular form of gynogenesis to be suitable for reverse breeding is that meiosis is still taking place in some if not all ovules of the ovary tissues taken as explant for the gynogenese tissue culture.

Other culture techniques that allows in vitro manipulation prior to the stage in which meiotic recombination takes place are also suitable for use in the invention.

In the above the haploids were the result of meiosis. However, it is also possible to start with somatic cells for the production of haploid cells.

Accordingly, in yet another preferred embodiment of the invention, the generation of plants containing unrecombined original parental chromosomes can be achieved by treatment of plants, plant organs or plant cells with chemical compounds like caffeine which result in chromosomal separation within a cell without the help of spindle fibers. In most cases the chromosomes separate evenly into two groups which after cytokinesis leads to haploid cells. The chromosomes in these cells can be doubled e.g. by colchicine in case spontaneous doubling has not been taken place already and regenerated into plants.

As the chromosomes separate without recombination, their constitution is still the same as in the original parent. Furthermore, as haploid cells are formed, doubling of the chromosomal number leads to fully homozygous plants. However the distribution of the chromosomes is random and therefore the resulting homozygous plants can contain all possible combinations of maternal and paternal chromosomal pairs.

This method is a specific embodiment of reverse breeding wherein somatic cells are used to produce progenitor cells which contain a haploid number of chromosomes which are unrecombined. This method is thus a form of reverse breeding in which there is no need to suppress meiotic recombination. This demonstrates that reverse breeding is a novel breeding concept which can be effectuated by seemingly different approaches.

Once according to the present invention a silencing construct has been prepared, which upon expression in a target crop species modifies the expression of genes in a quantitative and/or qualitative way which can result in the formation of viable, haploid spores that contain a full set of chromosomes which have not been subjected to meiotic recombination or which have been subjected to a reduced frequency of meiotic recombination as compared to the situation in which these genes are not modified, such construct needs to be transformed into the crop species which is to be treated according to the present invention.

Currently many different technologies exist which allow the delivery, stable integration and expression of DNA molecules in the genome of plants. These plant transformation technologies need to be combined with appropriate tissue culture technologies in order to regenerate a plant cell which has been transformed with a specific gene construct into a transgenic plant.

A well known plant transformation technology is based on the natural ability of a bacterial species called *Agrobacterium tumefaciens* to deliver and stably integrate a segment of DNA into the genome of a plant cell (Zambryski, P. et al (1989) Cell 56, 193-201). This piece of DNA, called T-DNA, is usually located on a plasmid which resides inside the bacterial cell. The natural T-DNA does not contain functions important for DNA delivery or integration and can in principle be any DNA. The plasmid which contains the T-DNA can be a binary vector (Bevan, M. (1984) Nucleic Acids Res. 12, 8711-8721) or a cointegrate vector (Fraley, R. T. et al (1983) Proc. Natl. Acad. Sci. USA 80, 4803-4807).

*Agrobacterium* cells which contain a plant transformation vector can be co-cultivated with explants derived from leafs or seedlings in order to deliver the T-DNA in cells present in the explant. (Horsch, R. et al (1985) Science 227, 1229-1231).

Incubation of the explants on tissue culture medium results in regeneration of cells present in the explant through organogenesis or embryogenesis. In many systems this regenerative step is preceded by a callus phase which is variable in length. Usually the T-DNA contains a selectable marker gene which upon expression in the transformed plant cell can confer resistance to a phytotoxic compound like the antibiotics kanamycin or hygromycin or the herbicides glyphosate or gluphosinate-ammonium. Addition of these phytotoxic compounds to the tissue culture medium during the regeneration of the cells of the explants prevents the outgrowth of untransformed cells or transformed cells which do not express the selectable marker gene to an insufficient extent.

Following this principle many transformation protocols have been developed for different crop species like potato (De Block, M. (1988) Theoretical and Applied Genetics 76, 767-774), lettuce (Michelmore, R. (1987) Plant Cell Reports 6, 439-442), tomato (McCormick, S. (1986) Plant Cell Reports 5, 81-84), pepper, cucumber (Trulson, A (1986) Theoretical and Applied Genetics 73, 11-15), carrot (Scott, R. J. and Draper, J. (1987) Plant Molecular Biology 8, 265-274), cauliflower (De Block, M. (1988) Plant Physiol. 91, 694-701), broccoli (Christy, M. C. and Earle, M. D. (1989) Australian Society of Plant Physiologists, 29th Annual Meeting, Abstract 40), eggplant (Guri, A. and Sink, K. C. (1988) J. of Plant Physiol. 133, 52-55), sugar beet (Gasser, C. S. and Fraley, R. T. (1989) Science 244, 1293-1299), asparagus (Conner, A. J. et al (1988) Ninth Australian Plant Breeding Conference, Proceedings. Agricultural Research Institute, Wagga Wagga, pp. 131-132 sunflower (Bidney, D. (1992) Plant Mol. Biol. 18, 301-313), oilseed rape (Thomzik J. E. (1995) Methods Mol. Biol. 44, 77-89, maize (Ishida, Y (1996) Nat. Biotechnol. 14, 745-750), wheat (Cheng, M. et al (1997) Plant Physiol. 115, 971-980), rice (Chan, M. T. (1993), Plant Molec. Biol. 22, 491-506).

Alternative methods to carry out plant transformation includes transformation of protoplasts in which DNA delivery is mediated by calcium, polyethylene glycol, or electroporation (Pazkowski et al (1984) EMBO J. 3, 2717-2722; Potrykus et al (1985) Molec. Gen. Genet. 199, 169-177; Fromm et al (1985) Proc. Natl. Acad. Sci. USA 82, 5824-5828; Shimamoto (1989), Nature 338, 274-276). Further methods include transformation mediated by silicon carbide whisker (Dunwell, J. M. (1999) Methods Mol. Biol. 111, 375-382), microinjection (Holm, P. B. et al (2000) Transgenic Res. 9, 21-32) or biolistics (Klein et al (1988) Proc. Natl. Acad. Sci. USA 85, 4305-4309; Becker, D (1994) Plant J. 5, 299-307). All these methods are useful in the present invention.

Transformants of crops that acquired a silencing construct are initially identified by their phenotype of resistance to the selective agent which has been used to obtain selective regeneration of transgenic cells expressing the selectable marker gene. Subsequently, the resistant transformants are further characterised molecularly to investigate the pattern of integration of the transformed DNA. Many techniques like polymerase chain reaction (PCR) or Southern blotting are available to carry out such an analysis and are well known to those skilled in the art (see for example techniques described Sambrook, J and Russell, D. W.: Molecular cloning, a laboratory manual (third edition, 2001), Cold Spring Harbor Laboratory Press, Cold Spring Harbor, N.Y.). Those transformants that contain a single, intact copy, of the transformed DNA are preferably selected for further analysis. However, transformants containing multiple copies of the transformed DNA may be useful as well. In order to analyse whether the transformed DNA in the genome of a transformant is expressed, the transformant can be analysed on RNA or protein species expected to be modified as a consequence of the presence of the transformed DNA.

Techniques well known to those skilled in the art enable to analyse the transgenic plant on the expression of the introduced gene or the effect the expression of the introduced gene has on the expression of a target gene by means of northern blotting, RT-PCR, in situ hybridisation, micro arrays, western blotting, enzymatic activity assays.

Phenotypic changes which result as a consequence of the modification of the expression of a target gene may occur as well but this is not necessarily the case. The fact that suppression of meiotic recombination through downregulation of a target gene can result in phenotypic changes is illustrated by the example of a knock out mutation in the AtSPO11-1 gene of *Arabidopsis* (Grelon, M. et al (2001) EMBO J. 20, 589-600). As a consequence of the reduced or zero expression of the AtSPO11-1 gene in *Arabidopsis*, the formation of bivalents at the end of the meiotic Prophase I is severely diminished. This can be explained by assuming that the stabilisation of the bivalents is reduced as a consequence of the absence of meiotic crossing over events and thereby chiasmata. Despite this abnormality, the chromosomes of this *Arabidopsis* mutant do segregate during meiosis, albeit in random direction which results in many unbalanced non-functional gametes. Macroscopically this can be observed by the fact that such mutant plants are semi-sterile i.e. a strong reduction of functional pollen en embryosacs are formed and thereby seed set is severely reduced. As this reduced fertility phenotype can be easily observed at the whole plant level, this phenomenon allows to identify plants in which a target gene has been modified either through genetic engineering, mutagenesis or chemical treatment. Although this phenotypic effect was found in this particular example it needs not necessarily always to be occurring to the same extent upon the modification of this or other target genes in other systems. In case semi-sterility occurs as a consequence of modification of target genes in the way as it has been described for AtSPO11-1 in *Arabidopsis*, the number of functional gametes is relatively lower as a function of the number of haploid chromosomes.

The % of functional gametes can be estimated by the formula $(\frac{1}{2})^n \times 100\%$ in which n is the haploid chromosomal number. In case the limitation in seed set is determined by the female gametes, the % of seeds that are formed can be calculated by the same formula. In case crops like sweet pepper (*Capsicum annuum* L.) with 12 haploid chromosomes show the same phenotype upon downregulation of the functional homologue of AtSPO11-1, such plant produces only $1/4096 \times 100\% = 0.024\%$ viable seeds. Such low amount of viable seeds jeopardizes the industrial applicability of suppression of meiotic recombination in plant breeding. This problem can be alleviated by regenerating spores of the plants in which meiotic recombination is suppressed into doubled haploid plants.

Thus, according to another aspect of the invention DH production is used to improve efficiency of the present method. The production of diploid plants out of haploid spores is a tissue culture technique which is used widely in plant breeding to accelerate the production of plant which are completely homozygous. Usually this technology is referred to as doubled haploid or DH technology.

In a haploid or monoploid plant, only one genome is present once. This means that all genes are present in a hemizyous state. In lower plant organisms, haploidy may be the predominant state; such is the case in the gametophyte of mosses. In crop plants however, haploidy is not the predominant state, except for the inconspicuous and parasitic gametophytes, the pollen grain, the pollen tube, and the embryo sac.

Haploid plants are usually sterile because of univalent chromosomes. However, doubled haploids that are obtained either by spontaneous doubling of the haploid chromosome content or achieved by other means such as chromosome doubling agents are among the most valuable tools in plant breeding. Doubled haploid plants are genetically homozygous and therefore the ultimate pure breeding lines that can theoretically only be achieved by many generations of inbreeding.

A haploid plant develops from haploid cells from an unfertilized ovule (gynogenesis), or haploid cells from anthers (androgenesis). The frequency of natural haploids is fairly low, about 1 per 1000 in the case of parthenogenesis and about 0.1 per 1000 in the case of androgenesis. Because of the low efficiency of natural occurring haploids, in vitro tissue culture methods have been worked out over the years to provide plant breeders with sufficient numbers of doubled haploids in order to partially or completely replace inbreeding. Anther and microspore cultures are well established techniques which are used for the production of homozygous lines in many crop species, such as maize (*Zea mays* L.): Gaillard et al. Plant Cell Reports: 10: 55-58 (1991), rice (*Oryza sativa* L.): Raina et al. Plant Cell Reports: 6: 43-45, (1987), oilseed rape (*Brassica napus*): Keller W. and Armstrong K. Z. Pflanzenzuchting 80, 100-108 (1978), barley (*Hordeum vulgare* L.): Ziauddin et al. Plant Cell Reports 9: 69-72 (1990), egg-plant (*Solanum melongena* L.): Tuberosa R. et al. Genet. Agr. 41; 267-274 (1987), broccoli (*Brassica oleracea* var. *Italica*): Takahata Y. and Keller W. Plant Science, 74, 235-242 (1991), safflower (*Carthamus tinctorius* L.): Plant Cell Reports 10: 48-51 (1991), asparagus (*Asparagus officinalis*) Pelletier G. et al. C. R. Ac. Sci. Paris. Ser. D 274, 848-851 (1972).

Haploids and doubled haploids can also be derived from gametophytic cells of the ovary in barley (*Hordeum vulgare* L.)) (San Noeum L. (Ann. Amelior. Plantes 26, 751-754 (1976)). Doubled haploid production via ovary cells is suitable for crop species that are in many cases not amenable for anther or microspore culture. Examples are sunflower (*Helianthus annuus* L.) Gelebart P. and San L. Agronomie, 7, 81-86 (1987), sugar beet (*Beta vulgaris* L.) Hosemans D and Bossoutrot D. Z. Pflanzenzucht 91: 74-77 (1983), melon (*Cucumis melo* L.) Cuny et al. Agronomie, 12, 623-630 (1992), watermelon (*Citrullus lanatus* (Thunb.)) Sari N et al. Scientia Horticulturae 82, 265-277 (1999), cucumber (*Cucumis sativus* L.) Dirks R. U.S. Pat. No. 5,492,827 (1995).

Doubled haploid plants derived from normal diploid donor plants are usually self pollinated and the resulting progeny is genetically identical and homogeneous, that is there should be no genetic segregation of alleles anymore. The combination of doubled haploid techniques with the suppression of crossing-over according to the invention provides very powerful new possibilities for plant breeding. All plants derived from doubled haploid techniques applied to plants (with any degree of heterozygosity) where crossing-over (chromosome recombination) is eliminated are fully homozygous. This means that a population of DHs derived from a plant in which recombination was suppressed, provides homozygous DH-plants that when crossed with another DH-plant from the same population results in generation of an F1 hybrid that is genetically identical to the individual plant that was used to generate the DH-population.

For example, cucumber has 7 chromosomes as a haploid set. In the theoretical case where a donor plant is heterozygous for genes on all chromosomes, and no crossing-over takes place, there are 128 different doubled haploid genotypes that possibly can occur, two of them being identical to the original parental plants that constituted the donor plant, in case the donor plant was derived from a cross between two homozygous original parental plants.

In comparison: after self-pollination of the same plant (heterozygous on all chromosomes and no crossing over taking place) there are 2187 different (diploid) genotypes that possibly can occur and the frequency of each of the original parental genotypes, in case the donor plant was derived from a cross between two homozygous original parental plants, is only 1 in 16384 (=(0.25)7) of diploid progeny plants.

To reach a sufficient probability of finding the genotype that one is looking for, the number of DH or inbred plants produced has to be multiplied with a factor. A reasonable factor is 3-4, giving a 95-98% chance of finding the desired genotype. Even with such a multiplier, the amount of DHs that should be produced are still industrially applicable, whereas in traditional self-pollination, the number of descendants to be produced amounts to very high quantities, that normally will not fit within the scope of a commercial breeding program.

Reconstruction of F1 hybrids by deducing the original parental ancestors and creating new parental lines can be useful in case one would like to develop alternative parents, that have better properties for seed or endosperm quality, for its commercial F1 seed production.

For reconstruction of an individual genotype, which is used for downregulation of recombination with subsequent production of doubled haploids, the genetic constitution is not relevant, and irrespective of the fact whether the plant is a hybrid or a plant with unknown genetic composition.

For instance in the case of cucumber there are theoretically 64 different combinations of two doubled haploid (DH) lines that when crossed provide progeny with a genotype identical to that of the original plant. Thus, in a set of only 48 cucumber DH's with nearly 100% certainty a pair of DH's can be found that after crossing reconstruct the original donor genotype. Even for an economically important crop like corn with 10 chromosomes, only 98 doubled haploid combinations have to be tested (see Example 2) to obtain parental lines that reconstruct their progenitor, with a probability of 99%.

The exact retrieval of specific parental lines is desired in the special case of the said "transfer of cytoplasm" from one line to another which is further described as example 12. The ultimate combination between recombination suppression and the production of doubled haploids followed by self pollination allows not only line selection but also provides new lines that resemble the original parental lines in all possible combination of chromosome combinations. As explained in the example with cucumber (Example 2) it is possible to produce new parental plants that when crossed reconstruct the donor material that was used for the derivation of the doubled haploids, whether or not the original parents from the donor material were homozygous or heterozygous.

In addition to such lines, other lines are generated, that have 6 chromosomes from one starting line and 1 chromosome from the other starting line that normally would generate the donor material (as a haploid set). When the donor material used for recombination suppression and doubled haploids, is an F1 hybrid that was created by crossing 2 homozygous lines (for instance derived from doubled haploids) and the said invention that is disclosed here is applied, then parental lines can be recovered that are identical to the two starting lines.

In addition, combinations for every single chromosome pair from one original parent with the other set of other chromosome pairs from the other original parent are generated. Combinations as these can be obtained for every individual chromosome pair but also with double pairs, triple pairs and so on can be obtained where the full set of chromosomes is then eventually completed. In practice, this means that parental lines are generated that are near to the original parental lines where only 1, or a limited number of the original parental chromosome pairs is substituted by a chromosome pair from the other original parent. This allows the generation of many more combinations of original parental lines than is possible in a traditional setting. Because of the absence of recombination and the fact that in diploid species the descendants of the DH technique are also fully homozygous, it is possible to detect genetic linkages.

In traditional genetics, the recombination frequency between 2 distinct genetic loci is used as a measure of genetic distance between these loci on a particular chromosome. The maximum frequency of recombination between any two genes is 50%, the same value that would be observed if the genes were on non-homologous chromosomes and assorted independently. 50% recombination occurs when the genes are so far apart on the chromosome that at least one crossing-over almost always occurs between them. According to the invention, due to the lack of crossing-over, induced by mutation, chemical treatment(s) or transgenic means whether or not stable or transient, all genes that reside on a particular chromosome are fixed in their respective allelic forms. Particularly in combination with doubled haploids, genes or loci located at the outer ends of the chromosomes co-segregate. Co-segregation is easily monitored if the genes encode visual markers, but currently available DNA fingerprinting technology association studies between DNA markers and important genes and DNA markers per se enhance the resolving power of linkage analysis. Examples of such DNA fingerprinting technologies are RFLP (Restriction Fragment Length Polymorphism (Beckmann, J. S. and Soller, M. (1983) Theor. and Appl. Genet. 67, 35-43)), RAPD (Random Amplified Polymorphic DNA (Welsh, J. and McClelland, M. (1990) Nucleic Acids Res. 19, 861-866)), SSR (Simple Sequence Repeat (Wu, K-S. and Tanksley, S. D. (1993) Mol. Gen. Genet. 241, 225-235)) and AFLP (Amplified Fragment Length Polymorphism, Vos, P et al (1995) Nucleic Acids Res. 23, 4407-4414)).

It is obvious that reverse breeding technology has the potential of creating new varieties in time-frames that never have been possible and utilizing the maximum variation that occurs within an existing gene pool.

According to a further aspect thereof, the invention relates to the improvement of efficiency for transfer of cytoplasmic male sterility in plants by using suppression of "crossing-over" or recombination. Cytoplasmic male sterility or CMS is a trait that is widely used in plant breeding. CMS is used for making F1 hybrid varieties in vegetable species such as carrot, cabbage, cauliflower, broccoli, brussels sprouts, chicory and endive, but also in agronomic species such as sugar beet and sunflower. CMS that is used in commercial plant breeding is inherited by the female parent, the phenotypic appearance of CMS (lack of pollen, brown anthers, petaloid anthers) can however also depend on nuclear factors that either may restore the male sterility or do not affect sterility (so called maintainers of CMS) In order to add the CMS trait to a specific fertile breeding line, the person skilled in the art knows that several back crosses are required in order to replace the majority of the nuclear genome from one line that harbours CMS by the genome that has to be converted to male sterility. The CMS donor line is maintained by back-crossing with isogenic male fertile line(s).

The CMS donor is made homozygous for a recessive mutation or a transgene that confers recombination suppression. The donor line is preferably genetically dissimilar from the line that has to be converted to male sterility for a large number of nuclear genetic markers so that the difference between the chromosomes of the CMS and the fertile donor can be more easily determined. In order to convert a desired inbred line or a pure line (homozygous or nearly homozygous) into a similar line but with a CMS background, a first cross is made by pollination of the said CMS homozygous recombination suppressed line with pollen of the desired line. The resulting F1 progeny contains CMS and 50% of the chromosomes of the desired line. In the meiosis of the resulting F1 plants, no recombination occurs as a result of the invention. This means that in the egg cells, independent chromosome assortment takes place. In the case of cabbage (*Brassica oleracea* L.) that has 9 chromosomes as a haploid set this means that 1 in 512 egg cells $((1/2)^9)$ have the same (but haploid) genetic composition as the said desired line that was used for pollinating the recombination suppressed CMS line. This egg cell is again fertilized by pollen of the desired line and the resulting seed is genetically identical for the nuclear genes to the original desired line, but now has acquired the CMS plasma. So in the second cross with the desired line, 1 in 512 seeds is isogenic to the desired line but said having acquired the CMS plasma of the donor line. In the newly achieved CMS/nuclear composition, no transgenic genes/plants have to be retained due to segregation of the transgenic locus that is responsible for suppression of meiotic recombination and because the transgenic plants are not retained.

Identification of the new CMS/desired nuclear line combination is very easy when DNA fingerprinting technology is used. In a preferred embodiment, genetic markers are used that have the capacity to identify every individual chromosome. In a preferred embodiment, one single homozygous recombination suppressed CMS-donor line can be used for making several (independent flowers) crosses with numerous said desired lines.

Surprisingly, with the present invention it is also possible to convert a CMS line into a maintainer line for those plant species in which restorer genes reside within the germplasm like in *Brassica* sp., carrot and radish. In order to apply the current invention with this objective, a fertile plant containing nuclear restorer genes and normal, non-CMS cytoplasm, is transformed with a construct that confers suppression of meiotic recombination. Transformants harbouring such construct preferably in a homozygous form are used as pollinator in a cross with a plant from a CMS line for which a maintainer line needs to be produced. The resulting hybrid plants will be male fertile as a consequence of the presence of the restorer genes and contain the construct in a heterozygous form. As the construct is genetically dominant, the chromosomes of the hybrid plants which are 50% derived from the original CMS line and 50% of the fertile plant containing the restorer genes, will not recombine during meiosis. Subsequently, such hybrid plant will be used as a pollinator in a cross with the original plant harbouring the restorer genes and the normal, non-CMS cytoplasm. Using molecular markers which allow specific detection of the chromosomes originating from the original CMS line, progeny plants are selected which contain a full complement of the chromosomes originating from the original CMS line. These plants are then used to produce doubled haploid plants which are selected for a full complement of chromosomes from the original CMS line using the same molecular markers. The resulting plants can be used as maintainer for the original CMS line.

Preferably, DNA fingerprinting is used to improve efficiency of the present invention. In a preferred embodiment of the present invention, DH technology is used in combination with suppression of recombination to obtain, in an efficient way, completely homozygous, diploid plants which have a full complement of chromosomes comprising a random combination of the chromosomes of the plants from which the double haploid plants were derived.

Although this embodiment is the most efficient one, the plants which are completely homozygous and which have a full complement of chromosomes comprising a random combination of the chromosomes of the plants in which meiotic recombination was suppressed can be identified using alternative approaches. These alternative approaches comprise DNA fingerprinting technologies, which enables the person skilled in the art to determine the level of polymorphisms that exists between genomes of any origin or complexity in a random fashion. In order to select the homozygous plants, seeds are produced by self-fertilization of a plant in which meiotic recombination is suppressed. The collection of these selfing seeds is used to grow the first inbred generation (S1). Within such S1, the total number of different genotypes that exists is $0.5(2^{2n}-2^n)+2^n$, where n is the haploid number of chromosomes. Within this population $2^n$ is the number of different but completely homozygous genotypes whereas all other plants are heterozygous for a variable number of chromosomes. In order to identify the homozygous plants, DNA that is extracted from these plants is analysed by a DNA fingerprinting technology. The relative level of polymorphism's that is measured for each plant of the S1 reflects the level of heterozygocity. This allows enriching the S1 population for plants with a relatively high level of homozygocity.

In order to identify the plants which are fully homozygous, marker alleles which have a known position on the genetic map of a given crop species can be tested for polymorphisms within the plant in which meiotic recombination is suppressed. In principle, when recombination is fully suppressed, the identification of a single polymorphic marker allele per chromosome which can be measured in a co-dominant fashion is sufficient to identify the homozygous plants in the S1. As the frequency of homozygous plants in an S1 decreases when the haploid number of chromosomes increases, this approach requires more input of resource when the crop species contains a higher haploid number of chromosomes. When a crop species has a number of n haploid chromosomes, the frequency of homozygous plants in an S1 is $2^{-n}$. Once these markers are available for each chromosome, it can be determined for each plant of the S1 whether these marker alleles are homo- or heterozygously present.

As during meiosis recombination is fully suppressed, homozygocity of a single marker allele is diagnostic for all loci on the same chromosome in terms of their homozygocity. This analysis allows identifying the homozygous plants in the S1 and further allows classifying the homozygous lines in complementation groups. Two plants are considered complementary when upon crossing of these plants, the genotype of the plant in which recombination was suppressed is fully recovered.

This analysis further allows producing F1 hybrids in which any predetermined set of chromosomes is present homozygously whereas all others are present heterozygously.

According to the invention endosperm or seed coat analysis from F1 hybrids can be used to determine maternal genotype. As described above, the availability of an assay to determine the presence of a minimum of one co-dominant marker allele per chromosome allows the determination of the zygocity of each chromosome of a plant of the S1 population produced on a plant in which meiotic recombination is suppressed. Within the group of homozygous plants those plants which have the same genotype as the mother plant of the plant in which meiotic recombination is suppressed can be identified by analyzing the DNA of the seed coat of the seed from which the plant was grown in which meiotic recombination is suppressed. The DNA in a seedcoat is of maternal origin and therefore, the available assays for the marker allele can be used to analyze the seedcoat DNA that reveals the identity of the maternal alleles. The data resulting from such analysis can be used to identify the homozygous plants in the S1 which have a genotype identical to the mother plant of the plant in which meiotic recombination is suppressed. The plants which have the same genotype as the father plant are those plants which are fully complementary to the mother plant.

As an alternative approach, the plants which have a genotype identical to the mother and father plants can be identified by analyzing the endosperm of the seed from which the plant was grown in which meiotic recombination is suppressed. As in endosperm tissues, the maternal genome is present in twofold over the paternal genome, a quantitative measurement of the presence of the marker alleles in a total nuclear DNA extract of the endosperm reveals the identity of the maternal and paternal alleles. The data resulting from such analysis can be used to identify the homozygous plants in the S1 which have a genotype identical to the mother or father plant of the plant in which meiotic recombination is suppressed.

In some species, 2n gametes from 2n parents (=unreduced gametes) arise by abnormalities during meiosis. In the special case of "second division restitution" unreduced gametes arise by an incomplete second division. The result is a dyad where both 2n cells are separated by a reduction cell wall. Gametes that are produced in such a way are homozygous in the case of the absence of crossing-over and recombination. In the present invention we show how to manipulate the phase of the meiosis in order to prevent that recombination takes place. Plants regenerated from 2n gametes produced by said second division restitution in the absence of recombination are the functional equivalent of doubled haploid plants. For SDR see fi. Hermsen J. In: The potential of meiotic polyploidization in breeding allogamous crops. Iowa State J. Res, Vol 58, No 4, pp 421-435 (1984). Mok D, and Peloquin S. Heredity 35, 295-302 (1975).

The invention is suitable for use in all non-human organisms, in particular in plants, especially in agriculture (potatoes, vegetables) and horticulture (vegetables, fruit, flowers) but also in potted plants, flower bed plants, shrubs, trees and fungi (mushrooms). Crop plants that may be subjected to the method of the invention comprise maize, wheat, rice, sugar beet, oilseed rape, ryegrass, sunflower, soybean, tomato, cucumber, spinach, pepper, petunia, potato, tobacco, eggplant, melon, carrot, radish, lettuce, vegetable *Brassica* species (cabbage, cauliflower, broccoli, kohlrabi, Brussels sprouts), leak, bean, endive, chicory, onion, potato, strawberry, radish, fennel, table beet, celery.

In many commercial plant species, such as many ornamental and woody plants, vegetative or clonal propagation is the exclusive or dominant way of commercial propagation. In breeding programs of these species, superior genotypes are identified in segregating populations, e.g. in an F2, and these are then maintained and multiplied by vegetative multiplication techniques.

In many of these species the method of vegetative propagation of (heterozygous) plants has become dominant because production of hybrid varieties through seeds (as is done in many annual and biannual crops) first requires several generations of inbreeding of parental lines, which in many woody and tree species would take too much time for any commercial program. By means of vegetative propagation superior genotypes are multiplied into a stock of genetically identical plants, and no time is "lost" to produce parental lines as is the case in seed-propagated hybrid crops.

However, there are also clear disadvantages of vegetative propagation. First, the logistics of producing plants through vegetative propagation is much more difficult than through seeds. Seeds can be stored easily, and often without problems for a long time. Seeds can be sown whenever commercial amounts of planting stock is required.

In the case of vegetatively propagated material it is much more difficult to respond to varying commercial needs for new planting stock. Vegetative production is labour and technology-intensive, and thus relatively expensive. Diseases, especially viruses, are a constant threat to vegetative multiplication. Many viruses are not transmitted by seeds, but are easily transmitted to clonal offspring obtained by vegetative reproduction techniques. For this reason some countries have strict quarantine regulations governing the importation of vegetatively produced plants.

Not all genotypes perform equally well in vegetative propagation. Some are difficult to propagate in this way. F.i. rooting ability of tree cuttings varies between species and clones.

Through reverse breeding according to the invention the genotype of the heterozygous clonally propagated plant can now be resynthesized and hybrid seeds with the said genotype provided.

In the context of the present invention the following definitions apply:

Starting organism: heterozygous organism that is used as a starting material in the method of the invention. The starting organism is not necessarily the direct result of a cross between two parents, but if so these parents are called the "original parents" and a line of such original parents is called an "original parental line".

(New) parent: a homozygous organism resulting from the method of the invention that can be used in a cross with a complementary (new) parent to reconstruct the original starting organism. A line of each (new) parent is called a "(new) parental line".

It should be noted that the use of the word "parent" or "parental line" in passages that do not directly describe the invention need not be references to a new parent or parental line.

Genotype: The genetic constitution of an individual organism.

Target gene: a gene residing within the genome of an organism which upon modification of its expression results in a meiotic process within said organism which is characterised by the formation of spores that contain a set of chromosomes which have not been subjected to meiotic recombination or which have been subjected to a reduced frequency of meiotic recombination as compared to the situation in which expression of said gene is not modified.

Functional homologues: Genes with the same or similar functions which can reside within one organism or can reside within organisms belonging to different biological species.

Suppression of meiotic recombination: An event which leads to the reduction, preferably absence of exchange of chromosome fragments between two paired chromosomes during meiosis.

The present invention is further elucidated in the Examples that follow and that are for illustration purposes only and are in no way intended to limit the invention.

EXAMPLES

Example 1

The Effect of Using Regeneration of Doubled Haploid Plants in Combination with Recombination Suppression For reverse breeding to be commercially feasible the efficiency of identifying fully homozygous plants which are present in the offspring of transformants in which meiotic recombination is suppressed is important. This example shows the effect, in terms of the degree of increased frequency of homozygous plants in the offspring population of plants in which meiotic recombination is suppressed, of the use of DH technology in combination with suppression of recombination as analysed for different crop species.

When recombination is suppressed, a fully heterozygous plant, which contains a haploid chromosome number of n, is able to produce a maximum number of $2^n$ genetically distinct gametes. When such a plant is self-fertilised, progeny plants have a maximum genetic variability of $0.5(2^{2n}-2^n)+2^n$ different genotypes. Within this population $2^n$ genotypically different but completely homozygous diploid plants exist whereas all other diploid plants are heterozygous for a variable number of chromosomes.

The application of DH technology in combination with suppression of meiotic recombination results exclusively in progeny plants, which are completely homozygous. As these plants are derived from microspores through e.g. androgenesis or megaspores through e.g. gynogenesis, the maximum number of genetically distinct diploid plants is identical to the maximum number of genetically distinct haploid gametes which can be produced by a plant in which meiotic recombination is suppressed which is $2^n$.

Table 1 shows the result of this analysis.

TABLE 1

The effect of DH technology on the efficiency of pure line recovery in a fully heterozygous plant (i.e. a plant that is heterozygous on every one of its chromosomes) in which meiotic recombination is suppressed, as a function of the haploid chromosomal number

| Haploid chromosomal number n | Example of a plant species | Maximum # of genetically distinct gametes | Maximum # of genetically distinct progeny plants after self-fertilisation (a) | Maximum # of genetically distinct, fully homozygous progeny plants after DH production (b) | Efficiency improvement expressed as a/b due to DH technology |
|---|---|---|---|---|---|
| 1 | | 2 | 3 | 2 | 1.5 |
| 2 | | 4 | 10 | 4 | 2.5 |
| 3 | | 8 | 36 | 8 | 4.5 |
| 4 | | 16 | 136 | 16 | 8.5 |
| 5 | Arabidopsis | 32 | 528 | 32 | 16.5 |
| 6 | spinach, corn salad | 64 | 2080 | 64 | 32.5 |
| 7 | cucumber, barley, scorzonera | 128 | 8256 | 128 | 64.5 |
| 8 | alfalfa, onion | 256 | 32896 | 256 | 128.5 |
| 9 | cauliflower, lettuce, sugar beet, carrot, broccoli, | 512 | 131328 | | 256.5 |

TABLE 1-continued

The effect of DH technology on the efficiency of pure line recovery in a fully heterozygous plant (i.e. a plant that is heterozygous on every one of its chromosomes) in which meiotic recombination is suppressed, as a function of the haploid chromosomal number

| Haploid chromosomal number n | Example of a plant species | Maximum # of genetically distinct gametes | Maximum # of genetically distinct progeny plants after self-fertilisation (a) | Maximum # of genetically distinct, fully homozygous progeny plants after DH production (b) | Efficiency improvement expressed as a/b due to DH technology |
|---|---|---|---|---|---|
| 10 | cabbage, radish, endive maize, asparagus, sorghum, Chinese cabbage, cocoa | 1024 | 524800 | | 512.5 |
| 11 | banana, watermelon, celery, parsley, fennel, common bean | 2048 | 2098176 | | 1024.5 |
| 12 | tomato, pepper, melon, potato, tobacco, rice, egg plant | 4096 | 8390656 | | 2048.5 |
| 13 | cotton | 8192 | 33558528 | | 4096.5 |
| 14 | Durum wheat, pea, lentil | 16384 | 1.34E+08 | | 8192.5 |

This analysis shows that for most if not all crops the use of DH technology has a profound effect on the efficiency of the recovery of homozygous plant as compared with the offspring obtained through self fertilization of the transformants in which meiotic recombination is suppressed.

As inferred from this analysis, the efficiency improvement depends on the haploid chromosomal number of a given plant species and ranges from one to three orders of magnitude (i.e. 10× to 1000×). It is concluded that the combined use of meiotic recombination suppression and DH technology significantly improves the commercial and practical feasibility of the method of the invention.

Example 2

Analysis of the Probability of Finding in a Number k of DH-plants from a Starting Plant in which Recombination was Fully Suppressed a Complementary Combination of DH Plants, that After Crossing can Resynthesize the Genotype of the Starting Plant, as a Function of the Chromosome Number n The present invention teaches the combined use of meiotic recombination suppression in combination with a technology for efficiency improvement like DH technology to enable the conversion of a heterozygous plant into an F1 hybrid variety by means of crossing parental lines obtained by the present invention as such.

In this example the analysis is shown of the probability of finding at least one complementary combination of two doubled haploid plants (a combination that after crossing can 'resynthesize' the starting plant), as a function of the haploid chromosomal number n of a given plant species and the number k of DH-plants produced from a heterozygous starting plant in which meiotic recombination is fully suppressed.

When the haploid chromosomal number of a given crop species is expressed as n, the maximum number of genotypes which are obtained from a plant of that crop species in which meiotic recombination is fully suppressed and from which double haploid plants are produced is $2^n$. The probability that one randomly chosen pair of double haploid plants from this population, upon crossing, results in an F1 hybrid which has a genotype identical to genotype in which recombination has been suppressed (original genotype) is $\frac{1}{2}$ (because $2^n/(2^n)^2$).

In case a total number of k doubled haploid plants is produced, there exists a number of $\frac{1}{2} \cdot k \cdot (k-1)$ combinations of 2 genetically distinct doubled haploid plants which can be crossed. The probability for any randomly chosen combination of 2 DH's that they are complementary (can resynthesize the original genotype after crossing) is $(\frac{1}{2})^n$. Thus the probability for any randomly chosen combination of 2 DH's that they are not complementary is $1-(\frac{1}{2})^n = 2^n-1)/2^n$. In case of k doubled haploids, $\frac{1}{2} \cdot k \cdot (k-1)$ combinations can be made and therefore the probability that within this DH-population no complementary DH's can be found is $((2^n-1)/2^n)^{(1/2k(k-1))}$ and therefore the probability of that at least one complementary combination of two DH's can be found is $1-((2^n-1)/2^n)^{(1/2k(k-1))}$.

Using this formula the number of doubled haploid plants can be calculated for each crop species which need to be pair wise crossed in order to maximise the probability to find the original genotype. The result of this analysis is shown in Table 2.

TABLE 2

The probability of finding at least one combination of two complementary DH's, using the 'reverse breeding' technology, as a function of the haploid chromosome number n and the number of available randomly produced doubled haploid plants k

| n/k | 2 | 4 | 8 | 16 | 24 | 32 | 48 | 64 | 128 | 256 |
|-----|-------|-------|-------|-------|-------|-------|-------|-------|-------|-------|
| 7   | 0.008 | 0.046 | 0.197 | 0.610 | 0.885 | 0.980 | 1.000 | 1.000 | 1.000 | 1.000 |
| 9   | 0.002 | 0.012 | 0.053 | 0.209 | 0.417 | 0.621 | 0.890 | 0.981 | 1.000 | 1.000 |
| 11  | 0.000 | 0.003 | 0.014 | 0.057 | 0.126 | 0.215 | 0.424 | 0.626 | 0.981 | 1.000 |
| 12  | 0.000 | 0.001 | 0.007 | 0.029 | 0.065 | 0.114 | 0.241 | 0.388 | 0.863 | 1.000 |

This analysis shows that the original genotype is resynthesized as an F1 hybrid according to the present invention with high probability using 48 doubled haploid plants for cucumber, 128 for cauliflower and 256 for tomato, melon and sweet pepper.

Example 3

Molecular Cloning and Characterization of the Target Genes DMC1, SPO11 and MSH5 from *Arabidopsis thaliana, Brassica oleraceae, Brassica carinata, Lycopersicon esculentum, Solanum melongena* and *Nicotiana tabacum*

Total DNA is extracted from plant tissues using the Genelute Plant Genomic DNA Kit (Sigma-Aldrich, Zwijndrecht, the Netherlands). The PCR reaction was carried out using a total amount of 30 ng DNA after which the reaction products were analysed on a 1% agarose gel. Total RNA is extracted from plant tissues using the commercially available RNeasy Plant Mini Kit from Qiagen (Valencia, Calif., USA). The purified RNA is subsequently treated with 1 µl of 10 units/µl Rnase-free DNase (Roche Diagnostics, Mannheim, Germany) in order to remove any residual DNA. The RT-PCR reaction is carried out using Superscript™ One-Step RT-PCR with Platinum® Taq from Invitrogen (Breda, the Netherlands), after which the reaction products are analysed on a 1% agarose gel. PCR products are cloned using the TOPO TA Cloning® system of Invitrogen (pCR®2.1-TOPO®) which is based on TA cloning and blue white colony screening.

1. Cloning of DMC 1

Based on the published gene sequence of DMC1 of *Arabidopsis thaliana*, AtDMC1 (GenBank Accession No. U76670), a primer combination was developed consisting of the following nucleotide sequences: forward primer 5'-ACA-GAGGCTTTTGGGGAATT-3' (SEQ ID NO:9) and reverse complement primer 5'-ACAGAGGCTTTTGGGGAATT-3' (SEQ ID NO:10). PCR analysis revealed a 380 bp cDNA fragment by RT-PCR from flower buds of *Arabidopsis thaliana* and an 1100 bp fragment from genomic DNA of *Arabidopsis thaliana*. This result is expected based on the known genomic sequence of the AtDMC1 gene. Sequence analysis of the cloned PCR products confirmed the identity of the cloned fragment as being part of the AtDMC1 gene as the obtained nucleotide sequence was identical to the published sequence. This result shows that the developed primer combination can be used effectively to specifically amplify a region of AtDMC1.

The same primer combination was used in an RT-PCR amplification reaction using RNA extracted from flower buds of *Brassica oleraceae* and *Brassica carinata*. For both plant species a 380 bp cDNA fragment was obtained which was cloned and sequenced. The *Brassica oleraceae* DMC1 gene is denominated BoDMC1 and its nucleotide sequence of the 380 bp cDNA fragment is shown in FIG. 1. The *Brassica carinata* DMC1 gene is denominated BcDMC1 and its nucleotide sequence of the 380 bp cDNA fragment is shown in FIG. 2.

Sequence alignment of the obtained sequences with the AtDMC1 gene showed a very high degree of identity of BoDMC1, BcDMC1 and AtDMC1. The percentages of identity between the different sequences are as follows: AtDMC1 and BoDMC1 95%, AtDMC1 and BcDMC1 93%, BcDMC1 and BoDMC1 96%.

The same primer combination was used in a PCR amplification reaction using genomic DNA extracted from tissues of *Lycopersicon esculentum, Solanum melongena* and *Nicotiana tabacum* which resulted in specific amplification products of 1100 bp for all 3 plant species. These fragments have a length which corresponds well to the length of the genomic fragment of *Arabidopsis thaliana* and were denominated LeDMC1 for *Lycopersicon esculentum*, SmDMC1 for *Solanum melongena* and NtDMC1 for *Nicotiana tabacum*. The fragments were cloned and sequenced, the result of which is shown in FIG. 3 for LeDMC1, FIG. 4 for SmDMC 1 and FIG. 5 for NtDMC 1. A BLAST analysis showed that the fragments contain regions with a high level of identity to AtDMC1 cDNA.

Together these data show that the cloned fragments of the solaneceous species are amplicons of the AtDMC1 orthologues which reside within the genome of these species.

2. Cloning of SPO11

In order to isolate DNA fragments of orthologous genes of SPO11, a primer combination was developed of which the primers correspond to a position of the *Arabidopsis thaliana* SPO11-1 (AtSPO11-1, ACCESSION AF-302928) genomic DNA which encodes a stretch of amino acids which is highly conserved between known SPO11 orthologues of different species. The primers have the following nucleotide sequences: forward primer 5'-AACGGGTTGGTGATGGG-3' (SEQ ID NO:11) and reverse complement primer 5'-CCATATGGATCACAGTCAAC-3' (SEQ ID NO:12). PCR analysis revealed a 350 bp cDNA fragment by RT-PCR from flower buds of *Arabidopsis thaliana*. This result is expected based on the known cDNA sequence of the AtSPO11-1 gene. Sequence analysis of the cloned PCR product confirmed the identity of the cloned DNA fragment being derived from the AtSPO11-1 gene, as the obtained nucleotide sequence was identical to the published sequence of AtSPO11-1. This result shows that the developed primer combination can be used effectively to specifically amplify a region of AtSPO11-1.

The same primer combination was used in an RT-PCR amplification reaction using RNA extracted from flower buds of *Brassica oleraceae* and *Brassica carinata*. For both plant species a 350 bp cDNA fragment was obtained which was cloned and sequenced. Sequence alignment of the obtained sequences with the AtSPO11-1 gene showed a very high degree of identity for both fragments with the AtSPO11-1 gene. The *Brassica oleraceae* SPO11 gene is denominated BoSPO11 of which the nucleotide sequence of the 350 bp cDNA fragment is shown in FIG. 6. The *Brassica carinata* SPO11 gene is denominated BcSPO11 of which the nucleotide sequence of the 350 bp cDNA fragment is shown in FIG. 7.

The percentages of identity between the PCR-fragments are as follows: AtSPO11-1 and BoSPO11 94%, AtSPO11-1 and BcSPO11 93%, BoSPO11 and BcSPO11 99%.

3. Cloning of MSH5

In order to isolate part of the *Arabidopsis thaliana* MSH5 gene use was made of the algorithm Codehop (Rose et al (1998) Nucleic Acids Research 26, 1628-1635). Based on conserved blocks of amino acids generated through alignment of MSH5 orthologues of *Caenorhabditis elegans*, *Mus musculus* and *Saccharomyces cerevisiae*, a primer combination is generated consisting of a specific clamp and degenerate core region. The following primer combination was used to amplify a region of the *Arabidopsis thaliana* genome: forward primer 5'-GTTTTTTATGGCTCATATTGGATGTT-TYGTNCCNGC-3' (SEQ ID NO:13) and reverse complement primer 5'-TCCACAGTATTAGTTCCCTTTCCAWAY-TCRTCDAT-3' (SEQ ID NO:14), where Y stands for C or T, N stands for A, T, G or C, W stands for A or T, R stands for A or G and D stands for A, G or T. PCR amplification using this primer combination of *Arabidopsis thaliana* genomic DNA resulted in a fragment of 220 bp which was cloned and sequenced. This sequence is given in FIG. 8.

A BLAST-X analysis revealed a high level of identity at the amino acid level of the translation product of the cloned fragment with known MSH5 amino acid sequences which is shown in FIG. 9. This demonstrates that this method can be used effectively to specifically isolate a portion of the MSH5 orthologue of *Arabidopsis thaliana* which was named AtMSH5.

Based on the nucleotide sequence of AtMSH5, a specific primer combination was made to amplify additional plant MSH5 sequences. This primer combination has the following sequence: forward primer 5'-TgTCCCGGCTGCATCGGC-CAAAATCGGC-3' (SEQ ID NO:15) and reverse complement primer 5'-GAATTCGTCAATCAAAATCAGT-GACCG-3' (SEQ ID NO:16) and generates a fragment of 170 bp on *Arabidopsis thaliana* genomic DNA.

This primer combination was then used in a PCR reaction using genomic DNA of *Brassica oleraceae*, *Lycoperisicon esculentum*, *Solanum melongena* and *Nicotiana tabacum* as template. For all plant species an amplified fragment of 170 bp was obtained.

These fragments were sequenced and the sequences were analyzed by BLAST-X. The result showed that the obtained fragments represent the MSH5 genes of the respective crop species. The genes were denominated as follows: *Lycoperisicon esculentum* MSH5: LeMSH5 (FIG. 14); *Solanum melongena* MSH5: SmMSH5 (FIG. 15); *Nicotiana tabacum* MSH5: NtMSH5 (FIG. 16) and *Brassica oleracea* MSH5: BoMSH5 (FIG. 13).

Example 4

Construction of RNA Interference (RNAi) Vectors for Downregulating Target Genes DMC1, SPO11 and MSH5

In order to downregulate the activity of a target gene in a particular plant species, use is made of RNA interference. For that purpose DNA fragments of the DMC1 and SPO11 of *Brassica carinata* and the MSH5 gene of *Arabidopsis thaliana* are inserted into pKANNIBAL (Wesley et al (2001) The Plant Journal 27, 581-590) such that upon expression in plants an RNA molecule is formed which folds back upon itself thus forming a hairpin structure that triggers the specific degradation of homologous RNA. The vector pKANNIBAL contains an intron positioned downstream of the CaMV 35S promoter and upstream form an octopine synthase polyadenylation signal. At either side of the intron a multiple cloning site is positioned which allows convenient insertion of the left and right arm of DNA corresponding to the RNA interference target in a inverted orientation relative to each other. Upon transcription the intron is removed by splicing and the left and right arm fold back on each other forming the double stranded RNA.

In order to generate a left arm for DMC1, SPO11 and MSH5, the gene fragments are reamplified from the vectors in which they have been cloned using primers which are extended with recognition sites for XhoI hybridising at the 5'-end of the gene fragment and KpnI hybridising at the 3'-end of the gene fragment.

The fragments which are generated by PCR using these primers is digested with XhoI and KpnI and subsequently inserted in pKANNIBAL digested with XhoI and KpnI. The resulting plasmids are denominated pRZ039 containing DMC1, pRZ040 containing SPO11 and pRZ041 containing MSH5.

Subsequently, the right arms are prepared similarly but using a different set of primers which generate a XbaI site at the 5' end of the gene fragment and a HindIII site at the 3'-end of the gene fragment. Upon digestion of the right arms they are inserted into the vectors containing the corresponding left arm resulting in pRZ042 for DMC1, pRZ043 for SPO11 and pRZ044 for MSH5.

Figure 11:
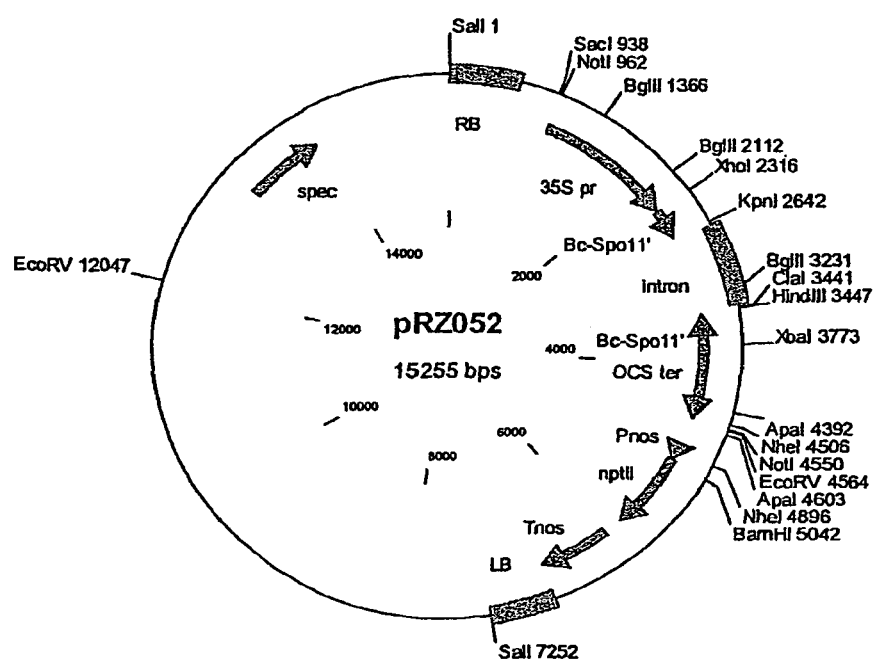
FIG. 11 is a Map of pRZ52. RB=right border, LB=left border, spec=spectinomycin/streptomycin resistance, 35S pr=CaMV 35S promoter, Bc-SPO11=BeSP011, OCS-ter=octopine synthase promoter, Pnos=nopaline synthase promoter, NPTII=neomycin phosphotransferase II, Tros=nopaline synthase polyadenylation signal.
Figure 12:
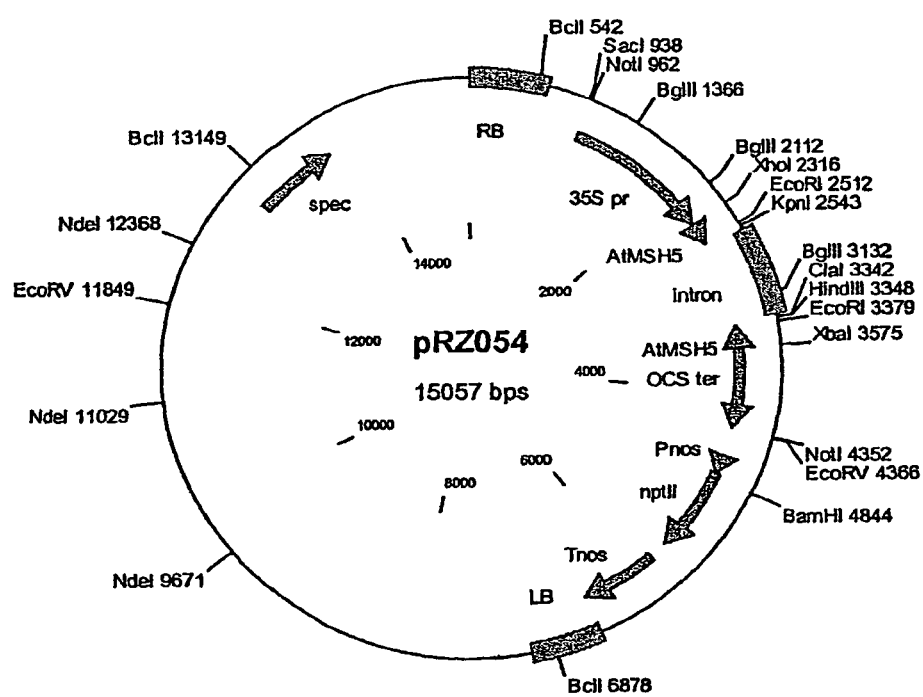
FIG. 12 is a Map of pRZ54. RB=right border, LB=left border, spec=spectinomycin/streptomycin resistance, 35S pr=CaMV 35S promoter, AtMsH5=AtMSH5, OCS-ter=octopine synthase promoter, Pnos=nopaline synthase promoter, NPTII=neomycin phosphotransferase II, Tnos=nopaline synthase polyadenylation signal.

As a final step the complete hairpin cassettes, containing the DMC1, SPO11 and MSH5 sequences as inverted repeat, are inserted separately as a NotI fragment into the NotI site of a T-DNA of a binary vector called pART27 which contains the neomycin phosphotransferase II gene as selectable marker for plant transformation. The integrity of the T-DNA was confirmed by sequence analysis. The resulting binary vectors, denominated pRZ051 for DMC 1 (FIG. 10), pRZ052 for SPO11 (FIG. 11) and pRZ054 for MSH5 (FIG. 12) are transferred into *Agrobacterium tumefaciens* using a triparental mating procedure with the helper plasmid pRK2013 (Ditta et al (1980) Proc. Natl. Acad. Sci. USA 77, 7347-7351).

Because of the high level of sequence identity of the BcDMC1 and BcSPO11 and the AtMSH5 sequence with the respective orthologous genes, the constructs are effective in the downregulation of the target genes within all species of the Cruciferaceae family. Moreover, as the LeDMC1, SmDMC1 and the NtDMC1 sequences show regions of high similarity to the BcDMC1 cDNA, pRZ051 are also effective in solaneceous species. In addition, given the similarity of the BcDMC1 to the DMC1 gene of rice the BcDMC1 sequences can be used even more broadly i.e. also in monocotyledonous plant species like for instance rice, wheat, barley and maize.

In general, the above described method can be used to make constructs containing DNA fragments which are homologous to other target genes that need to be down-regulated.

Example 5

Transformation of *Arabidopsis thaliana* with pRZ051, pRZ052 and pRZ054

*Agrobacterium tumefaciens* strain C58 (ATTC 33970) containing either one of the plant transformation vectors pRZ051, pRZ052 or pRZ054 is grown overnight in LB medium containing streptomycin (100 mg/L) and spectinomycin (300 mg/L) to select for the vectors and rifampicin (40 mg/L) and gentamycin (25 mg/L) to select for the *Agrobacterium tumefaciens* C58 background at 29° C.

In order to produce transgenic *Arabidopsis* plants, the floral dip method is used, as described by Desfeux et al. (2000) Plant Physiology 123, 895-904. The bacterial cells are resuspended in floral dip solution (50 g sucrose+500 µl Silwett L-77 surfactant (Helena Chemical Comp. Fresno, Calif., USA) per liter MilliQ™ (Millipore, Etten-Leur, the Netherlands). Bolting plants, containing multiple floral buds, are submerged into the dipping solution containing the *Agrobacterium* cells at an Optical Density (OD) between 1.0 and 1.5 during 5-10 seconds with gentle agitation.

After inoculation, the plants are contained in a plastic container to keep high humidity under low light conditions for a day and subsequently, seeds are grown on the plants.

Transformants are selected by germinating surface sterilised seeds in 0.1% agarose layered upon half-strength MS plates containing 50 mg/L kanamycin. Kanamycin resistant seedlings are transferred to soil in a greenhouse.

In total 51 kanamycin resistant seedlings/construct were grown to mature plants which were analysed by PCR for the presence of the T-DNA. Primer combinations were designed which specifically amplify either the NPTII gene (NEO-FORW+NEO-REV), the region from the CaMV 35S promoter to the intron (35S-F1+RNAi-intr-R1) and the region from the intron to the OCS terminator (RNAi-intr-F1+OCS-R1). The sequences of these primer combinations are given below. The result of this analysis showed that in all plants specific amplification signals were obtained for the mentioned primer combinations which confirms the transgenic status of the kanamycin resistant seedlings and which shows the presence of the RNA interference constructs. Sterile plants have been confirmed from this experiment.

```
NPTII:
                                        (SEQ ID NO: 21)
NEO-FORW 5'-CAG ACA ATC GGC TGC TCT GAT GCC-3'

(SEQ ID NO: 22)
NEO-REV 5'-CGT CAA GAA GGC GAT AGA AGG CG-3'

Promotor-Intron:
                                        (SEQ ID NO: 23)
35S-F1 5'-AgAATgCTgACCCACAgATggTTA-3'

(SEQ ID NO: 24)
RNAi-intr-R1 5'-CTTCgTCTTACACATCACTgTCAT-3'

Intron-Terminator
                                        (SEQ ID NO: 25)
RNAi-intr-F1 5'-ATgACAgTgATgTgTAAgACgAAg-3'

(SEQ ID NO: 26)
OCS-R1 5'-TggCgCTCTATCATAgATgTCgCT-3'
```

Example 6

Transformation of Crop Plants and Production of Homozygous Lines

1. Constructs

The constructs described in Example 4 were used for the transformation of various crop plants by means of *Agrobacterium*. *Arabidopsis* constructs can be used in *Brassica*. Optionally, the genes of the constructs of Example 4 can be exchanged with the homologous endogenous gene of the relevant crop as given in the description. In addition, functional homologues can be used.

2. Transformation and DH Production 2.1. Maize

Incorporation of silencing constructs in the genome of maize are performed according to EP-801134, U.S. Pat. No. 5,489,520 or EP 97114654.3 which teaches *Agrobacterium* transformation of DSM6009 corn protoplasts. The silencing construct introduced into the maize cells confers an inhibitory effect when the regenerated transformed plant undergoes meiosis on recombination so that recombination is omitted or significantly reduced. As a consequence of the activity of the said inhibitory nucleic acids, numerous egg cells respectively pollen, were found to contain a chromosome number that deviates from the normal number and are partially or completely inadequate for either being fertilised (egg cells) or as a functional pollinator (pollen). In that case the transformants are either male or female sterile or the seed production is lowered.

Some microspores respectively egg cells did however contain a normal, functional haploid set of chromosomes that results from a meiosis where no or little recombination has taken place (as compared to wild type). These haploid microspores respectively egg cells are the starting material for making doubled haploids.

Haploids in maize are obtained from microspores as described by Pescitelli S and Petolino J (1988) Plant Cell Reports 7: 441-444; Coumans M et al., (1989) Plant Cell Reports 7: 618-621; Pescitelli S et al., (1989) Plant Cell Reports 7: 673-676. Buter B (1997) In: In Vitro Haploid Production in Higher plants, vol 4, 37-71. Kluwer Academic Publishers. Eds. S Jain, S Sopory & R Veilleux.

Subsequently diploid plants are produced from haploid plants by either spontaneous diploidization or chemically. Preferably, plants are selected that contain a single copy of the transgene. Due to reduction or elimination of recombination during meiosis some of these plants are homozygous for all alleles. On average, 50% of those doubled haploids contain the transgene that confers the recombination downregulation whereas 50% is free of transgenic nucleic acids.

Alternatively, haploid maize plants were produced following natural and artificial pollination with a haploid inducer as described by Rotarenco V (2002) Maize Genetics Cooperation News Letter 76: 16. In this case seeds were obtained that contain haploid embryos. Also in this case, only haploids that have lost the transgene due to segregation from the hemizygous donor material are retained.

Chromosome doubling is performed as described by Wan, Y & Widholm, J (1995) Z. Pflanzenzuecht 114: 253-255.

Plants that contain one copy of the transgene (established by means of Southern blot or so-called Invader technology) are withheld for use in crosses in order to avoid repetitive transformation events.

2.2. Rice

Rice genetic transformation is carried out according to Zhang Bing and Wei Zhiming (1999) Acta Phytophysiologica Sinica vol 25, no 4, or Datta and Datta (1999) In: Methods in molecular biology vol 111, 335-347 Eds. Robert D. Hall, Humana press Totowa, N. J.

After the said inhibitory DNA that confers inhibition of recombination during meiosis is incorporated in the rice genome, preferentially regenerants containing one copy of the inhibitory DNA are further used for making doubled haploids by means of anther culture, microspore culture and ovary culture according to Gosal S et al., (1997) In: In Vitro Haploid Production in Higher plants, vol 4, 1-35. Kluwer Academic Publishers. Eds. S Jain, S Sopory & R Veilleux.

2.3. Onion

The method of the invention is especially powerful in crops with a relatively low chromosome number. Onion (2n=2x=16) is therefore an excellent species for practical application of the present invention. Transformation in onion is performed according to protocols developed by Eady (1995) New Zealand Jounal of Crop and Horticultural Science, vol 23: 239-250.

Again plants containing one copy of the silencing DNA construct conferring inhibition of recombination during meiosis are retained and used as starting material for making doubled haploids according to Keller E and Korzun L. (1996) In: In Vitro Haploid Production in Higher plants, vol 3, 51-75. Kluwer Academic Publishers. Eds. S Jain, S Sopory & R Veilleux.

Subsequently diploid plants are produced from haploid plants by either spontaneous diploidization or chemically.

2.4. Cucumber

Cucumber with a haploid chromosome number of 7 is also a crop species where the invention is very powerful. The silencing constructs are introduced by means of *Agrobacterium* transformation in embryogenic callus as disclosed in EP-97114654.3 or by *Agrobacterium* transformation via direct organogenesis according to Ganapathi A and Perl-Treves R. In: ISHS Acta Horticulturae 510: VII Eucarpia Meeting on Cucurbit Genetics and Breeding; Mohiuddini A et al., (2000) Plant Tissue Cult 10 (2): 167-173.

After identification of transformants with only one copy of the transformed DNA that confers inhibition of recombination during meiosis, haploids are produced by means of gynogenesis as described in EP 0 374 755.

Subsequently diploid plants are produced from haploid plants by either spontaneous diploidization or chemically.

2.5. Sugar Beet

Transformation in sugar beet is performed as described by Hall R et al., (1996) Nature Biotechnology 14, 1133-1138.

Subsequently, doubled haploids are obtained as described in Pedersen H and Keimer B (1996) In: In Vitro Haploid Production in Higher plants, vol 3, 17-36. Kluwer Academic Publishers. Eds. S Jain, S Sopory & R Veilleux.

2.6. *Brassica* sp.

Transformation of various *Brassica* species is performed according to Moloney M et al., ((1989) Plant Cell Reports 8, 238-242) for *Brassica napus*; Metz T et al., ((1995) Plant Cell Reports 15, 287-292) for broccoli (*Brassica oleracea* var. *italica*) and cabbage (*B. oleracea* var. *Capitata*); and Bhalla P and Smith N ((1998) Molecular Breeding 4, 531-541) for cauliflower (*Brassica oleracea* var. *Botrytis*).

Doubled haploids were prepared according to Palmer C et al., (1996) In: In Vitro Haploid Production in Higher plants, vol 2, 143-172. Kluwer Academic Publishers. Eds. S Jain, S Sopory & R Veilleux.

2.7. Eggplant

Transformation of *Solanum melongena* is performed according to Leone et al. (1993) In: Biotechnology in Agriculture and Forestry, vol. 22, Plant Protoplasts and Genetic Engineering III, Y. P. S. Bajaj ed., Springer-Verlag (Heidelberg), pp. 320-328. Doubled haploids are prepared according to Dumas de Vaulx, R. and Chambonnet (1982) Agronomie 2: 983-988. Subsequently, diploid plants are produced from haploid plants by either spontaneous diploidization or chemically.

Example 7

Reverse Breeding for Transfer of CMS (Cytoplasmic Male Sterility)

CMS is one of the most prominent tools for plant breeding in the production of F1 hybrid varieties. Farmers demand a uniform phenotype (and therefore preferentially genotype) of the plant from the seeds they buy. In order to achieve this, self pollination of the seed producing plant has to be excluded. In order to do this emasculation of the female line by hand is required which is a costly and error prone activity.

In some crops natural male sterility offers a better and more efficient alternative. Such crops are for instance but not limited to rice, sugar beet, carrot, and *Brassica* spp. Until 1970 nearly all of the hybrid corn was produced using T cytoplasm for F1 production.

A selected pure line as a result of traditional plant breeding or obtained by the aid of doubled haploid methodology that has been propagated by self-fertilization is converted to male sterility by making a cross of this line to a line that is a carrier of cytoplamatic sterility.

Preferably, the pollinator and the CMS donor are characterized genetically by using genetic markers such as but not limited to AFLP, RFLP, RAPD, Invader etc as is well known to the persons skilled in the art.

In this Example the male sterile line is suppressed for recombination, as exemplified in the other examples. When this suppression is achieved transgenically then lines are selected that are homozygous for the transgene. The F1 progeny that results from the cross of the pollinator with the CMS acceptor inherits 50% of the chromosomes form both parents. Egg cells produced by plants of this generation are formed in the absence of recombination which means that when the haploid chromosome number is 9 which is the case for cauliflower, carrot and sugar beet, 1 egg cell in 512 of the egg cells that contain a full chromosome set inherits exactly the same chromosomal constitution as the egg cells or the pollen from the pollinator. This means that after successful pollination already the second back cross gives rise to seeds in which the chromosomal content of the original pollinator has been transferred in the cytoplasmic environment of the CMS line.

The identification of this isogenic line is performed with the aid of molecular makers.

Example 8

Using the Invention to Produce a Maintainer Line (B-line) from a Homozygous CMS-line (A-line)

A maintainer or B-line of *Daucus carota, Brassica oleracea* or *Raphanus sativus* was produced starting from a homozygous cytoplasmic male sterile line or A-line using the present invention. In many crops cytoplasmic male sterile (CMS) mother lines are used to produce hybrid seeds. The CMS mother line (A-line) is maintained by backcrossing with a line that has the same or highly similar nuclear constitution, but has normal plasma, and thus is male fertile (B-line). Often a new A-line is produced by crossing elite male fertile genotypes with CMS-plants, choosing those combinations that maintain the CMS in the offspring (B-lines, i.e. lines with 'maintainer-capacity', i.e. lines that lack restorer genes), and backcrossing the CMS progeny several times with the original B-line until the resulting A-line is genetically very similar to the B-line. Surprisingly in species in which restorer genes are present (*Brassica*, carrot, radish) reverse breeding can provide a corresponding B-line from any homozygous CMS plant by means of the breeding scheme given below. The symbols use in the breeding scheme are as follows:

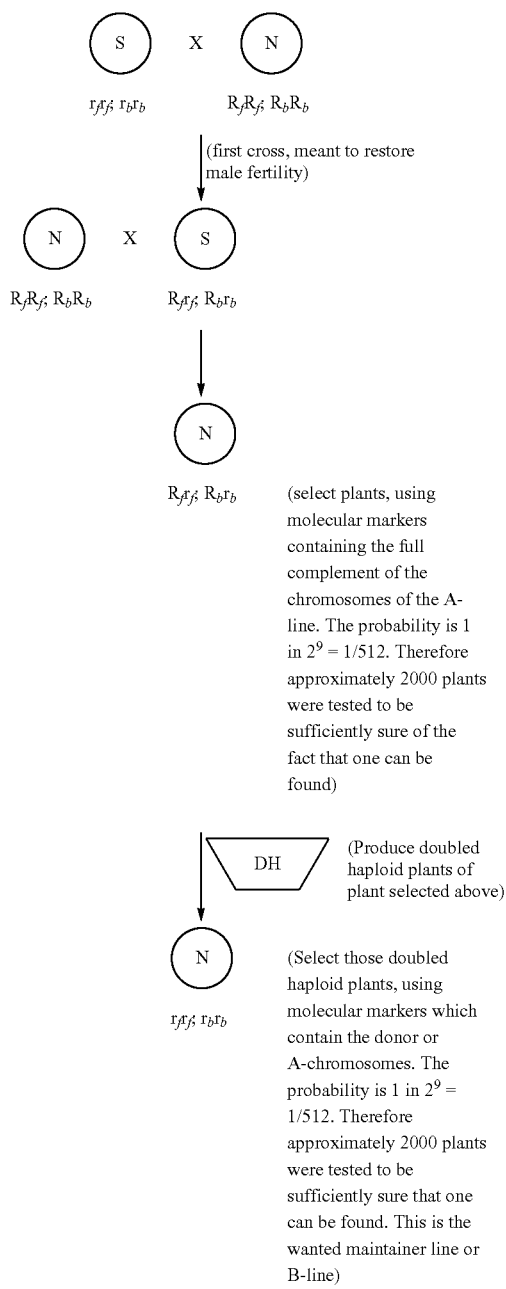

$R_f$ = Restorer gene present
$r_f r_f$ = Maintainance capacity present/no restorer gene present
$R_b R_b$ or $R_b r_b$ = Suppresser of activity of target gene present
$r_b r_b$ = Suppresser of activity of target gene absent
N = normal, fertile cytoplasm
S = cytoplasmic male sterile plasm Example 9

Reverse Breeding Using Caffeine Treatment of Meristematic Cells

Seeds of *Brassica oleraceae* are surface sterilised by submerging them for 30 minutes in 6% solution of hypochlorite (commercial bleach, 1.5% NaOCl final concentration) after which they are thoroughly rinsed with sterile milliQ. Subsequently, the seeds are germinated on sterile, wet filter paper. The germinated seeds which show the primary root are soaked into a 70 mmol/L caffeine solution for a period of 2 hours after which the seeds were rinsed with sterile milliQ.

Subsequently the seeds are allowed to recover by placing them on sterile, wet filter paper for 24 hours. The optimal treatment for different plant species can differ and should be established by testing different concentrations of caffeine, different incubation times and different recovery times. After the treatment, the meristematic cells are taken into tissue culture by preparing the root tips and transferring them onto MS-medium containing 0.5 µg/l 2,4-D (2,4 dichlorophenoxy acetic acid) into the dark for a period of 2 weeks to induce callus.

After this callus induction, plants are regenerated by placing the callus onto medium containing 0.5 mg/L BA (16/8 hours light/dark, 25° C.). After regeneration the shoots are analysed molecularly for the presence of each of the haploid chromosomes by using genetic markers for each chromosome, preferably markers that are polymorph for each set of chromosomes. Haploid shoots containing a full complement of chromosomes are doubled by treatment with colchicine.

Example 10

Reverse Breeding by Chemical Induction of Aneuploidy Followed by Selection of Haploid Plants Containing a Complete Set of Chromosomes Flowering plants of *Brassica oleraceae* which contain young floral buds which are in a pre-meiotic state are treated with different chemical compounds known to induce aneuploidy selected from etoposide, podophyllin, benomyl, maleic hydrazide, atrazine, butachlor, APM, griseofulvin, vinblastin-sulphate, diazepam, colchicine, cadmiumchloride, econazole, pyrimethamine, thiabendazole, thimerozal or nocodazole according to C. B. S. R. Sharma (1990) Mutagenesis 5, 105-125 and references therein; and Sandhu et al. (1991) Mutagenesis 6, 369-373.

The chemical is applied by dipping the pre-meiotic floral buds into a solution or by spraying a solution onto the pre-meiotic floral buds. As the developmental stage of the floral buds of a plant may be variable and therefore the effectiveness of the applied chemical may be different for each individual floral buds, the treatment is repeated a number of times to enhance the probability of exposing the appropriate developmental stage for a maximal number of floral buds. In addition to the chemical compound, the solution contains a surfactant like Agralin (Syngenta, Roosendaal, the Netherlands) (0.25 ml/100 ml).

After application, the treated buds are labelled and grown to the stage optimal for microspore regeneration which on average occurs when the buds have a length of approximately 3 millimeter. Purified microspores are harvested from these buds and given a stress treatment of 2 days at 32° C. which is optimal to induce sporophytic development of the haploid cells.

After regeneration the shoots are analysed for the presence of each of the haploid chromosomes as described above. Haploid shoots containing a full complement of chromosomes are doubled by treatment with colchicine.

Example 11

Using the Invention to Provide Seed Propagated Varieties in Species that Now are Commercially Multiplied by Vegetative Propagation Techniques In many commercial plant species, e.g. many ornamental and woody plants, vegetative or clonal propagation is the exclusive or dominant way of commercial propagation. In breeding programs of these species, superior genotypes are identified in segregating populations, e.g. in an F2, and these are then maintained and multiplied by vegetative multiplication techniques, which are well known to the person skilled in the art. In many of these species the method of vegetative propagation of (heterozygous) plants has become dominant because production of hybrid varieties through seeds (as is done in many annual and biannual crops) first requires several generations of inbreeding of parental lines, which in many woody and tree species would take too much time for any commercial program. By means of vegetative propagation superior genotypes are multiplied into a stock of genetically identical plants, and no time is "lost" to produce parental lines as is the case in seed-propagated hybrid crops.

However, there are also clear disadvantages of vegetative propagation. The logistics of producing plants through vegetative propagation is much more difficult than through seeds. Seeds can be stored easily, and often without problems for a long time. Seeds can be sown whenever commercial amounts of planting stock is required. In the case of vegetatively propagated material it is much more difficult to respond to varying commercial needs for new planting stock. Furthermore, vegetative production is labour- and technology-intensive, and thus relatively expensive. Diseases, especially viruses, are a constant threat to vegetative multiplication. Many viruses are not transmitted by seeds, but are easily transmitted to clonal offspring obtained by vegetative reproduction techniques. For this reason some countries have strict quarantine regulations governing the importation of vegetatively produced plants. In addition, not all genotypes perform equally well in vegetative propagation. Some are difficult to propagate in this way. E.g. rooting ability of tree cuttings varies between species and clones. Through reverse breeding according to the invention the genotype of the heterozygous clonally propagated plant can now be resynthesized and hybrid seeds with the said genotype provided.

Transformation of *Malus domestica* is performed according to Yepes, L. M. and H. S. Aldwinckle. 1989. Genetic transformation of apple. Abstract. UCLA Symposium on Plant Gene Transfer. Park City, Utah, Apr. 1-7, 1989.

Doubled haploids are prepared according to Zhang et al. (1992) Plant Breeding 108:173-176. Subsequently, diploid plants are produced from haploid plants by either spontaneous diploidization or chemically.

Example 12

Using Reverse Breeding to Improve Seed Production in Hybrid Crops

Production of hybrid seeds at a commercial scale can encounter a large number of difficulties which leads to a reduced quality or quantity of seeds. This can hinder in turn the commercialisation of high quality hybrids varieties. These difficulties can be caused by a number of different factors like an intrinsic poor seed production capacity of the maternal line of the hybrid or a difference in flowering time, crop height or flower morphology (preventing insects of carrying out cross pollination because of a preference for one flower type over the other) of the maternal and paternal lines of the hybrid.

By applying reverse breeding according to the invention to a hybrid which has excellent agronomic properties but poor seed production characteristics (which makes the commercialisation of the hybrid less attractive or even impossible), this hybrid can be resynthesized using lines which differ from the original maternal and paternal lines. By selecting a combination of lines which allows the production of commercial seeds of both high quality and quantity, the commercialisation of the hybrid becomes economically feasible or more attractive.

The invention claimed is:

1. A method for producing homozygous plants from a heterozygous starting plant, comprising:
    at least partially preventing or suppressing recombination by interfering with at least one target gene involved in double strand breaks, chromosome pairing and/or strand exchange while allowing the heterozygous starting plant to produce haploid cells, whereby a limited number of genetically different haploid cells are thus obtained;
    creating homozygous plants from the haploid cells by forming doubled haploid cells; and
    selecting from the plants those having the desired set of chromosomes,
    wherein the interfering with the at least one target gene includes destabilizing the at least one target gene mRNA or transcript.

2. The method of claim 1 wherein the at least one target gene mRNA or transcript is destabilized by nucleic acid molecule(s) complementary to the at least one target gene mRNA or transcript selected from the group consisting of antisense RNA, an RNAi molecule, an RNA oligonucleotide, and a Virus Induced Gene Silencing (VIGS) molecule.

3. The method of claim 2 wherein the nucleic acid molecule(s) complementary to the at least one target gene mRNA or transcript comprises a VIGS molecule.

4. The method of any one of claims 1-3, wherein the at least one target gene is selected from the group consisting of SPO11, RHD54/TID1, DMC1, SAE3, RED1, HOP1, HOP2, REC8, MER1, MRE2, ZIP1, ZIP2, MEI5, RAD51, RAD52, RAD54, RAD55, RAD57, RPA, SMC3, SCC1, MSH2, MSH3, MSH6, PMS1, SOLODANCERS, HIM6, CHK2, MER2, MEI4, REC102, REC104, REC114, MEK1/MRE4, RAD50, MRE11, XRS2, and their functional homologues.

5. The method of any one of claims 1-3, further comprising crossing the homozygous plants to produce a progeny plant.

6. The method of any one of claims 1-3, further including transferring cytoplasmic male sterility (CMS).

7. The method of any one of claims 1-3, including making parental lines to produce F1 hybrid seeds.

* * * * *

UNITED STATES PATENT AND TRADEMARK OFFICE
CERTIFICATE OF CORRECTION

PATENT NO. : 8,692,067 B2
APPLICATION NO. : 13/253697
DATED : April 8, 2014
INVENTOR(S) : Robert Helene Ghislain Dirks et al.

Page 1 of 1

It is certified that error appears in the above-identified patent and that said Letters Patent is hereby corrected as shown below:

TITLE PAGE under (63) Related U.S. Application Data, the recitation of "Continuation of application No. 10/487,468, filed as application No. PCT/EP02/09526 on Aug. 23, 2002, now Pat. No. 8,242,327" is to be changed to --Continuation of application No. 10/487,468 filed April 4, 2006 now Pat No. 8,242,327, which is a National Stage Entry of PCT/EP02/09526 filed August 23, 2002--

Signed and Sealed this
Fifth Day of May, 2015

Michelle K. Lee
*Director of the United States Patent and Trademark Office*

SEQUENCE LISTING

<160> NUMBER OF SEQ ID NOS: 31

<210> SEQ ID NO 1
<211> LENGTH: 380
<212> TYPE: DNA
<213> ORGANISM: Brassica oleracea
<220> FEATURE:
<223> OTHER INFORMATION: Partial nucleotide sequence of BoDMC1

<400> SEQUENCE: 1

```
aagaggcttt tggggaattt aggtctggga aaactcaatt agcacatacc ctttgtgtca      60
ccacgcagct gcctacaagc atgaaaggtg ggaatgggaa agtggcttac attgacactg     120
agggaacctt ccgccctgat cggattgtcc aaattgctga aagatttgga atggatcccg     180
gagctgtgct tgacaatatc atttatgctc gtgcttacac ctatgagcat cagcacaact     240
tgcttcttgg ccttgctgca aaaatgtccg aggaaccatt taagattctg attgttgact     300
caatcattgc tttattccga gtggatttca ctggaagagg agaactcgca gaccgccagc     360
aaaaactagc tcagatgctt                                                  380
```

<210> SEQ ID NO 2
<211> LENGTH: 381
<212> TYPE: DNA
<213> ORGANISM: Brassica carinata
<220> FEATURE:

<223> OTHER INFORMATION: Partial nucleotide sequence of BcDMC1

<400> SEQUENCE: 2

| | | | | | |
|---|---|---|---|---|---|
| acagaggctt | ttggggaatt | caggtctggg | aaaactcagt | tagcacatac | cctttgtgtc | 60 |
| accacgcagc | tgcctacaag | catgaaaggt | gggaatggga | agtggctta | cattgacact | 120 |
| gaaggaacct | tccgccctga | tcgaatcgtc | cccattgctg | aaagatttgg | aatggatcca | 180 |
| ggagctgtgc | ttgacaatat | catctatgct | cgtgcttaca | cctatgagca | tcagtacaac | 240 |
| ttgcttcttg | gccttgctgc | aaaaatgtct | gaggaaccat | ttaagattct | gattattgac | 300 |
| tcgatcattg | ctttattccg | agttgatttc | actggaagag | gggaactcgc | agaccgccag | 360 |
| caaaaactag | ctcagatgct | t | | | | 381 |

<210> SEQ ID NO 3
<211> LENGTH: 1061
<212> TYPE: DNA
<213> ORGANISM: Lycopersicon esculentum
<220> FEATURE:
<223> OTHER INFORMATION: Partial nucleotide sequence of LeDMC1

<400> SEQUENCE: 3

| | | | | | |
|---|---|---|---|---|---|
| agaggctttt | ggggaattca | ggtaaggatc | aatcaaatat | tgtattaacc | ttgtggtaga | 60 |
| gctttagtag | aatatttcat | ctaactctgc | tgtatgaact | atttattcag | atctggaaag | 120 |
| acacaacttg | ctcatactct | ctgtgtctct | actcaggttc | agctctgatc | ttagtcagaa | 180 |
| gcaatggaac | atcattaccg | tctagattac | ttctgatcct | ttatatgctt | tatgctgaat | 240 |
| catgatatca | ttcggagttt | aacaagattg | ccaattgatt | tgtctgattt | actgcagctt | 300 |
| ccgactagta | tgaaaggagg | gaatggaaaa | ggtggcttac | attgatactg | agggaacatt | 360 |
| gtatccttgc | taatatttcg | caactcatga | aaattcaaac | tagcacctat | tactctcttc | 420 |
| attaagtagc | agctgcagaa | actcaagtga | atgctgcttc | cttccatttt | atctttttc | 480 |
| ctcaaccaaa | gcgtactaca | gtcggccaga | tcgtgttgtt | cccattgctg | aaagatttgg | 540 |
| aatggacgct | ggagcagttc | ttgacaatgt | aaagggtctt | ttacacccac | catttaatca | 600 |
| tctactgctc | tttgtttagt | gtactgattt | cttatccttt | ctttccttat | tatgtgatca | 660 |
| gatcatttat | gctcgcgcat | acacatatga | acatcaatat | aacctgcttc | ttggtctggc | 720 |
| agcaaaaatg | gctgaagagc | ctttcagact | tctggtgaaa | gccacatcat | ctgctttatc | 780 |
| ttgaataaga | ccattactgg | cggcagttgt | ctcagatact | gaaattttac | ttgcagattg | 840 |
| ttgactctgt | gattgcttta | tttcgagtgg | atttcactgg | aagaggagag | cttgcagacc | 900 |
| gtcaggtata | actaaataca | caagcataat | atttgattaa | ttaaaaacct | atctctgata | 960 |
| tttatctgtg | ttgagaagaa | cctgcaatca | cctgttctgg | tagactttt | ctgaatgctt | 1020 |
| atgccttctt | gccatttcag | caaaaactag | ctcagatgct | t | | 1061 |

<210> SEQ ID NO 4
<211> LENGTH: 1079
<212> TYPE: DNA
<213> ORGANISM: Solanum melongena
<220> FEATURE:
<223> OTHER INFORMATION: Partial nucleotide sequence of SmDMC1

<400> SEQUENCE: 4

| | | | | | |
|---|---|---|---|---|---|
| acagaggctt | ttggggaatt | caggtaagga | tcaactaact | attgctttag | ctttgtggta | 60 |
| gaagcattag | tagaatttta | catctaactg | tctgaatgaa | ctatttattc | agatctggaa | 120 |
| agacacaact | tgctcatact | ctctgtgtct | ctactcaggt | tcacctctga | tcttagtcag | 180 |

```
aagcaatgga acatctttac cttctagatt actcctgatc ctttatatgc tttatgctta      240
atcatggtat catcctgaat ttaacaagat tgccaattga tttgtctggt ttattgcagc      300
ttcctacaag catgaaagga gggaatggaa aggtggctta cattgacacc gagggaacat      360
tgtatccttg ctaatatttc tctactcata cagcatgaac tacaaactag ctcctattag      420
tctcttcact aagtagcagc tgcagaagct caagagaatt cttcccttcc tatattttc      480 cctcaactaa gtgtactata gtcggccaga tccgtgtggt gcccattgct gaaagatttg      540
gaatggacgc aggagcagtt cttgacaatg ttaagtgtct tttattcact catttaatca      600
tctactgctc tttgttcagc gtactgattt ctcagctgat tttctaatcc ttccttcct      660 aatcacgtga atgaatcaga tcatttatgc tcgcgcatac acatacgaac atcaatacaa      720
cttgcttctt ggtttggcag caaaaatggc tgaagagcct ttcagacttc tggtgaaagc      780
cacaacttct ggtttatcct gaataagtcc attactgatg gcagttgtct cagatactga      840
aattttactt gcagatcatt gactccgtga ttgctttatt tcgagtggat ttcactggaa      900
gaggagagct tgcagatcgc caggtatgaa atacagagca tgatagctga tttattaagt      960
tcccatttat tgctatttac ggttgtgtta agaagacctg caatcacctg ttctgatgtg     1020
ctatcttttg aatgcctaca ctttcttgcc atttacagca aaaactagct cagatgctt      1079
```

<210> SEQ ID NO 5
<211> LENGTH: 1086
<212> TYPE: DNA
<213> ORGANISM: Nicotiana tabacum
<220> FEATURE:
<223> OTHER INFORMATION: Partial nucleotide sequence of NtDMC1

<400> SEQUENCE: 5

```
agaggctttt ggggaattca ggtaacaatc aactaattat cgttttacct ttggtgtaga       60
agcattatct gaatatttca tctaactctc tgctgaatga acaatttatt cagatctgga      120
aagacacaac ttgctcatac tctatgtgtc tctactcagg ttcacctctg atcttagtta      180
gaagcaatga agttttgac cttctaaatc cctccttatc ctttatatgc tttagactta      240
atcatggtat catccagaac atgacaagag tgtcaattcg tttgtctgat ttatttcagc      300
ttcctactag catgaaagga gggaatggaa aggtggctta cattgatact gagggaacgt      360
tgtatccttg ctgatatttc cttactcatg tagcatcaat aatcaaacta gcacttaaaa      420
gtctcctcat gaagtagcag ctgtagaaac aaaagagaat gcttccttcc attttatctt      480
gtttcttcaa cctaagtgta ctatagtcgg ccagatcgtc ttgtgcccat tgctgaaaga      540
tttggaatgg acgcaggagc tgttcttgac aatgtaaagc gtcttttgac cctcatttaa      600
tgatctctcc ctctctttgt ttagcttact gattttttcag ctgatttctt atcattccct      660 tttccccttta tgatgtgaat tcaccagatc atttatgctc gtgcatacac atacgaacat      720
cagtacagcc tgcttttttgg tctggcagca aaaatggctg aagagccttt cagacttctg      780
gtgaaagcca caacttccag tttatcctga atagaatcat tgctaatgga ctcatatact      840
gaaatattac ttgcagattg ttgactctgt gattgcttta tttcgagtgg atttcactgg      900
aagaggagaa cttgcagaac gtcaggtata acaaaataca gaaatatgat atttgattta      960
taagttcctg tctcttgata tttatctttg ttctaagaag agcctgcaat cacctattct     1020
aaatatgttt taatttgagt gactgcacct tcttgccata tccagcaaaa actagctctg     1080
atgctt                                                                1086
```

<210> SEQ ID NO 6

```
<211> LENGTH: 320
<212> TYPE: DNA
<213> ORGANISM: Brassica oleracea
<220> FEATURE:
<223> OTHER INFORMATION: Partial nucleotide sequence of BoSPO11

<400> SEQUENCE: 6
aacgggttgg tgatggggtg gttaaagttt agggaagctg aaggaagtt tgattgttta      60 agcagcctga atactgcatt tcccgttcct gttcttgtag aggaagtcga agatattgtt     120
agtttggcag agtacatact ggtggtggaa aaggaaacag tattccagcg tttagcaaat    180
gacatgtttt gcaagacgaa ccgctgcatc gtcgtcacag gaagaggcta tcctgatgtc    240
tctacaagaa ggttcttgcg actcctgatg gagaagttgc aactacctgt gcattgtcta    300
gttgactgtg atccatatgg                                                320

<210> SEQ ID NO 7
<211> LENGTH: 318
<212> TYPE: DNA
<213> ORGANISM: Brassica carinata
<220> FEATURE:
<223> OTHER INFORMATION: Partial nucleotide sequence of BcSPO11

<400> SEQUENCE: 7
aacgggttgg tgatggggtg gttaaagttt agggaagctg aaggaagtt tgattgttta      60 agcagcctga gtactgcatt tcccgttcct gttcttgtag aggaagtcga agatattgtt     120
agtttggcag agtacatact ggtggtggaa aaggaaacag tattccagcg tttagcaaat    180
gacatgtttt gcaagacgaa ccgctgcatc gtcgtcacag gaagaggcta tcctgatgtc    240
tctacaagaa ggttttttgcg actcctgatg gagaagttgc aactacctgt gcattgtcta   300
gttgactgtg atccatat                                                  318

<210> SEQ ID NO 8
<211> LENGTH: 221
<212> TYPE: DNA
<213> ORGANISM: Arabidopsis thaliana
<220> FEATURE:
<223> OTHER INFORMATION: Partial nucleotide sequence of AtMSH5

<400> SEQUENCE: 8 gtttttatg gctcatattg gatgttttgt cccggctgca tcggccaaaa tcggcctagc      60
cagagagatt ttcacgcgac tctattcgga agagtcgacg cacaacagcc agtcgtcatt    120
ccagttggaa ttgatacaaa tgagtcgaat attgtcatcg tcgtcggacc ggtcactgat    180
tttgattgac gaattcggaa agggaactaa tactgtggat g                        221

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
acagaggctt tggggaatt                                                  20

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
```

```
                          primer

<400> SEQUENCE: 10
acagaggctt ttggggaatt                                                    20

<210> SEQ ID NO 11
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
aacgggttgg tgatggg                                                       17

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
ccatatggat cacagtcaac                                                    20

<210> SEQ ID NO 13
<211> LENGTH: 36
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (31)..(31)
<223> OTHER INFORMATION: a, c, t or g
<220> FEATURE:
<221> NAME/KEY: modified_base
<222> LOCATION: (34)..(34)
<223> OTHER INFORMATION: a, c, t or g

<400> SEQUENCE: 13 gtttttatg gctcatattg gatgtttygt nccngc                                   36

<210> SEQ ID NO 14
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
tccacagtat tagttccctt tccawaytcr tcdat                                   35

<210> SEQ ID NO 15
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
tgtcccggct gcatcggcca aaatcggc                                           28
```

```
<210> SEQ ID NO 16
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
gaattcgtca atcaaaatca gtgaccg                                           27

<210> SEQ ID NO 17
<211> LENGTH: 168
<212> TYPE: DNA
<213> ORGANISM: Brassica oleracea
<220> FEATURE:
<223> OTHER INFORMATION: Partial nucleotide sequence of BoMSH5

<400> SEQUENCE: 17
tgtcccggct gcacggccaa atcggccta gccagagaga ttttcacgcg actctattcg        60
gaagagtcga cgcacaacag ccagtcgtca ttccagttgg aattgataca aatgagtcga      120
atattgtcat cgtcgtcgga ccggtcactg attttgattg acgaattc                  168

<210> SEQ ID NO 18
<211> LENGTH: 165
<212> TYPE: DNA
<213> ORGANISM: Lycopersicon esculentum
<220> FEATURE:
<223> OTHER INFORMATION: Partial nucleotide sequence of LeMSH5

<400> SEQUENCE: 18
tgtcccggct gcgccaaaat cggcctagcc agagagattt tcacgcgact ctattcggaa       60
gagtcgacgc acaacagcca gtcgtcattc agttggaat tgatacaaat gagtcgaata      120
ttgtcatcgt cgtcggaccg gtcactgatt ttgattgacg aattc                     165

<210> SEQ ID NO 19
<211> LENGTH: 168
<212> TYPE: DNA
<213> ORGANISM: Solanum melongena
<220> FEATURE:
<223> OTHER INFORMATION: Partial nucleotide sequence of SmMSH5

<400> SEQUENCE: 19
tgtcccggcg catcggccaa atcggccta gccagagaga ttttcacgcg actctattcg        60
gaagagtcga cgcacaacag ccagtcgtca ttccagttgg aattgataca aatgagtcga      120
atattgtcat cgtcgtcgga ccggtcactg attttgattg acgaattc                  168

<210> SEQ ID NO 20
<211> LENGTH: 168
<212> TYPE: DNA
<213> ORGANISM: Nicotiana tabacum
<220> FEATURE:
<223> OTHER INFORMATION: Partial nucleotide sequence of NtMSH5

<400> SEQUENCE: 20
tgtcccggct gcatcggcca aatcggcct agccagagag attttcacgc gactctattc        60
ggaagagtcg acgcacaaca gccagtcgtc attccagttg gaattgatac aaatgagtcg      120
aatattgtca tcgtcgtcgg accggtcact gattttgatt gacgattc                  168

<210> SEQ ID NO 21
<211> LENGTH: 24
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 21
cagacaatcg gctgctctga tgcc                                              24

<210> SEQ ID NO 22
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
cgtcaagaag gcgatagaag gcg                                               23

<210> SEQ ID NO 23
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
agaatgctga cccacagatg gtta                                              24

<210> SEQ ID NO 24
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
cttcgtctta cacatcactg tcat                                              24

<210> SEQ ID NO 25
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
atgacagtga tgtgtaagac gaag                                              24

<210> SEQ ID NO 26
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
tggcgctcta tcatagatgt cgct                                              24

<210> SEQ ID NO 27
<211> LENGTH: 72
<212> TYPE: PRT
<213> ORGANISM: Artificial Sequence
<220> FEATURE:
```

<223> OTHER INFORMATION: Description of Artificial Sequence: Synthetic
      polypeptide
<220> FEATURE:
<221> NAME/KEY: MOD_RES
<222> LOCATION: (47)..(62)
<223> OTHER INFORMATION: Any amino acid

<400> SEQUENCE: 27

Phe Met Ala His Ile Gly Cys Phe Val Pro Ala Ala Ser Ala Lys Ile
1               5                   10                  15

Gly Leu Ala Arg Glu Ile Phe Thr Arg Leu Tyr Ser Glu Glu Ser Thr
            20                  25                  30

His Asn Ser Gln Ser Ser Phe Gln Leu Glu Leu Ile Gln Met Xaa Xaa
        35                  40                  45

Xaa Xaa Xaa Xaa Xaa Xaa Xaa Xaa Xaa Xaa Xaa Xaa Xaa Xaa Glu Phe
    50                  55                  60

Gly Lys Gly Thr Asn Thr Val Asp
65                  70

<210> SEQ ID NO 28
<211> LENGTH: 72
<212> TYPE: PRT
<213> ORGANISM: Saccharomyces cerevisiae

<400> SEQUENCE: 28

Tyr Leu Ala Gln Ile Gly Cys Phe Val Pro Ala Glu Arg Ala Arg Ile
1               5                   10                  15

Gly Ile Ala Asp Lys Ile Leu Thr Arg Ile Arg Thr Gln Glu Thr Val
            20                  25                  30

Tyr Lys Thr Gln Ser Ser Phe Leu Leu Asp Ser Gln Gln Met Ala Lys
        35                  40                  45

Ser Leu Ser Leu Ala Thr Glu Lys Ser Leu Ile Leu Ile Asp Glu Tyr
    50                  55                  60

Gly Lys Gly Thr Asp Ile Leu Asp
65                  70

<210> SEQ ID NO 29
<211> LENGTH: 72
<212> TYPE: PRT
<213> ORGANISM: Homo sapiens

<400> SEQUENCE: 29

Phe Met Ala Leu Val Gly Ser Phe Val Pro Ala Glu Glu Ala Glu Ile
1               5                   10                  15

Gly Ala Val Asp Ala Ile Phe Thr Arg Ile His Ser Cys Glu Ser Ile
            20                  25                  30

Ser Leu Gly Leu Ser Thr Phe Met Ile Asp Leu Asn Gln Val Ala Lys
        35                  40                  45

Ala Val Asn Asn Ala Thr Ala Gln Ser Leu Val Leu Ile Asp Glu Phe
    50                  55                  60

Gly Lys Gly Thr Asn Thr Val Asp
65                  70

<210> SEQ ID NO 30
<211> LENGTH: 72
<212> TYPE: PRT
<213> ORGANISM: Mus musculus

<400> SEQUENCE: 30

Phe Met Ala Leu Val Gly Ser Phe Val Pro Ala Glu Glu Ala Glu Ile
1               5                   10                  15

```
Gly Val Ile Asp Ala Ile Phe Thr Arg Ile His Ser Cys Glu Ser Ile
                20                  25                  30

Ser Leu Gly Leu Ser Thr Phe Met Ile Asp Leu Asn Gln Val Ala Lys
            35                  40                  45

Ala Val Asn Asn Ala Thr Glu His Ser Leu Val Leu Ile Asp Glu Phe
        50                  55                  60

Gly Lys Gly Thr Asn Ser Val Asp
65                  70

<210> SEQ ID NO 31
<211> LENGTH: 70
<212> TYPE: PRT
<213> ORGANISM: Caenorhabditis elegans

<400> SEQUENCE: 31

Phe Leu Ser His Ile Gly Ser Phe Val Pro Ala Arg His Ala Lys Ile
1               5                   10                  15

Gly Ile Val Asp Arg Ile Val Thr Arg Met Phe Thr Val Asp Ser Val
                20                  25                  30

Leu Asp Gly Met Ser Thr Phe Ala Lys Asp Val Glu Gln Val Ala Leu
            35                  40                  45

Ala Leu Arg Lys Ala Thr Gly Asn Ser Leu Val Ile Ile Asp Glu Phe
        50                  55                  60

Gly Lys Gly Thr Met Thr
65                  70
```